United States Patent
Wolfson et al.

(10) Patent No.: US 10,869,676 B2
(45) Date of Patent: Dec. 22, 2020

(54) SYSTEM FOR USE IN KNEE SURGERY

(71) Applicant: DEPUY IRELAND UNLIMITED COMPANY, County Cork (IE)

(72) Inventors: David Wolfson, Leeds (GB); Michael Rock, Pudsey (GB); Abraham Wright, Winona Lake, IN (US); Danny Rumple, Warsaw, IN (US)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 160 days.

(21) Appl. No.: 16/117,111

(22) Filed: Aug. 30, 2018

(65) Prior Publication Data
US 2019/0008524 A1 Jan. 10, 2019

Related U.S. Application Data

(63) Continuation of application No. 15/104,327, filed as application No. PCT/US2015/010573 on Jan. 8, 2015, now abandoned.

(30) Foreign Application Priority Data

Jan. 8, 2014 (GB) .................................. 1400287.7

(51) Int. Cl.
*A61F 2/38* (2006.01)
*A61B 17/15* (2006.01)
*A61F 2/30* (2006.01)

(52) U.S. Cl.
CPC ........ *A61B 17/155* (2013.01); *A61F 2/30767* (2013.01); *A61F 2/3859* (2013.01); *A61F 2002/3093* (2013.01)

(58) Field of Classification Search
CPC ................ A61F 2/3859; A61F 2/30767; A61F 2002/30879; A61F 2002/30891–30896; A61B 17/155
See application file for complete search history.

(56) References Cited

U.S. PATENT DOCUMENTS

| | | |
|---|---|---|
| 4,714,473 A | 12/1987 | Bloebaum |
| 5,080,674 A | 1/1992 | Jacobs |

(Continued)

FOREIGN PATENT DOCUMENTS

| | | |
|---|---|---|
| BE | 1020866 A4 | 6/2014 |
| DE | 19755776 C2 | 3/2000 |

(Continued)

OTHER PUBLICATIONS

Brazilian Search Report From Corresponding Brazalian Application No. BR112016015802-4, dated Mar. 16, 2020, 4 Pages.
(Continued)

*Primary Examiner* — Dinah Baria

(57) ABSTRACT

A femoral component (2) of a knee joint prosthesis has a bearing surface (4) for articulation with a tibial bearing surface and an opposite bone facing surface (6). The bone facing surface has anterior (18), posterior (20), distal (22), anterior chamfer (24) and posterior chamfer (26) portions. Medial (42, 52, 356) and lateral rails (40, 50, 350) are provided on the distal portion or on at least one of the anterior chamfer portion and posterior chamfer portions of the bone facing surface so that there is at least one recess (46, 54, 354, 360) between the rails.

6 Claims, 12 Drawing Sheets

(56) References Cited

U.S. PATENT DOCUMENTS

| | | |
|---|---|---|
| 6,749,638 B1 | 5/2004 | Saladino |
| 7,572,262 B1 | 8/2009 | Hoeppner |
| 7,628,818 B2 | 12/2009 | Hazebrouck et al. |
| 8,287,601 B2 | 10/2012 | Wagner et al. |
| 8,333,805 B2 | 12/2012 | Williams, III |
| 8,372,080 B2 | 2/2013 | May |
| 8,728,086 B2 | 5/2014 | Smith et al. |
| 8,808,297 B2 | 8/2014 | Stemniski |
| 8,871,142 B2 | 10/2014 | Smith et al. |
| 8,915,965 B2 | 12/2014 | Komistek |
| 8,926,709 B2 | 1/2015 | Lenz et al. |
| 8,968,412 B2 | 3/2015 | Wogoman et al. |
| 9,033,989 B2 | 5/2015 | Wolfson et al. |
| 9,114,012 B2 | 8/2015 | Wogoman |
| 9,173,744 B2 | 11/2015 | Donno et al. |
| 9,592,127 B2 | 3/2017 | Earl |
| 9,717,598 B2 | 8/2017 | Otto et al. |
| 2012/0109325 A1 | 5/2012 | Wagner et al. |
| 2013/0013077 A1 | 1/2013 | Metzger et al. |
| 2014/0005791 A1 | 1/2014 | Bonitati et al. |
| 2014/0257305 A1 | 9/2014 | Edwards et al. |
| 2014/0296929 A1 | 10/2014 | Stacey |
| 2015/0032218 A1* | 1/2015 | Landon .................. A61F 2/3094 623/20.35 |
| 2015/0088142 A1 | 3/2015 | Gibson |

FOREIGN PATENT DOCUMENTS

| | | |
|---|---|---|
| FR | 2625096 B3 | 3/1990 |
| JP | 04-166802 A | 6/2004 |
| JP | 2013537453 | 10/2013 |
| RU | 2187975 C1 | 8/2002 |
| WO | WO 0023010 A1 | 4/2000 |
| WO | WO 12059825 A1 | 5/2012 |
| WO | WO 1367859 A1 | 5/2013 |

OTHER PUBLICATIONS

Japanese Search Report for Corresponding Application No. 2016-545335, dated Oct. 23, 2018, 3 Pages.
International Search Report for Corresponding International Application No. PCT/US2015/010573 dated Mar. 30, 2015, 6 Pages.
Sigma Fixed Bearing Knees—Function With Wear Resistance, 2.5M0610 (0612-65-508) (Rev. 1) Printed 2010, 20 Pages.
Attune Surgical Technique—0M0000 (0612-59-508) (Printed 2011) 60 Pages.
Chinese Search Report for Corresponding Application No. CN 201580004155.5, dated Oct. 22, 2017, 5 Pages.
Search Report for Corresponding Application No. GB1400287.7, dated Aug. 6, 2014, 3 Pages.
Russian Search Report for Corresponding Application No. CN 2016131174/14 (048426), dated Jul. 19, 2018, 2 Pages.

* cited by examiner

SYSTEM FOR USE IN KNEE SURGERY

CROSS REFERENCE TO RELATED APPLICATION

This application is a continuation of U.S. patent application Ser. No. 15/104,327, filed Jun. 14, 2016, which is a National Stage 35 U.S.C. 371 of International Patent Application PCT/US15/10573 filed Jan. 8, 2015, which claims priority to United Kingdom Application No. 1400287.7, filed Jan. 8, 2014 (now abandoned), all of which are incorporated by reference in their entireties.

BACKGROUND OF THE INVENTION

This invention relates to a system for use in a surgical procedure on a patient's knee, which includes a femoral component of a knee joint prosthesis and a guide block for defining the locations of planes on which the anterior and posterior chamfer cuts can be performed relative to the plane of the distal resection cut.

Knee replacement surgery can be appropriate when the joint is damaged due to disease. It can also be appropriate when the joint is damaged as a result of trauma. Total knee replacement surgery involves replacement of the entire joint. Partial (or unicondylar or unicompartmental) knee replacement involves replacement of one compartment (medial or lateral) of the joint. Separate replacement of both compartments of a knee is sometimes referred to as a bicompartmental knee replacement.

The femoral component of a knee joint prosthesis is fitted to the femur after performing a series of cuts so that the end of the femur is appropriate shaped to fit the femoral component. For example, the cuts can include cuts on the anterior, distal and posterior faces of the femur, with an anterior chamfer cut between the anterior and distal faces and a posterior chamfer cut between the posterior and distal faces.

Joint prosthesis components can be fixed in place using a bone cement. EP-A-2574312 discloses a femoral component of a knee joint prosthesis which is intended to be fixed in place using a bone cement.

It can be preferred to fix a joint prosthesis components in place without the use of a cement. This can be achieved by appropriately adapting surfaces of the component so as to promote bone ingrowth. The component surfaces can be porous to facilitate ingrowth. This can be achieved by sintering beads to create a porous surface structure, for example as in components which are sold by DePuy Orthopaedics Inc under the trade mark POROCOAT. The component surfaces can be coated with a material which promotes formation of a strong physical connection with the bone tissue when bone is generated at the interface between the tissue and the coated surface. An example of such a material is the ceramic hydroxyapatite ($Ca_{10}(PO_4)_6(OH)_2$). FR-A-2625096 discloses a femoral component of a knee joint prosthesis in which the bone facing surfaces are provided by a metallic mesh.

It can be important to achieve fixation of a prosthesis component without cement to create bone surfaces which are arranged so as to achieve surface-to-surface contact over the entire area of the portions of the bone facing surfaces of the prosthesis component where interaction with ingrowing bone tissue is to take place to achieve fixation. Those portions will often be essentially planar. This can facilitate the formation of similarly configured surfaces on the bone.

WO-A-2013/067859 discloses a knee joint prosthesis in which the femoral component has reinforcing ribs on its bone facing surfaces to prevent it from deforming. A space between the ribs can receive bone graft material.

When a femoral component of a knee joint prosthesis is to be fixed in place through interaction with ingrowing bone tissue, it has been found to be preferable for that fixation to take place on the anterior, distal and posterior bone facing portions of the bone facing surfaces of the component. When the bone facing surface of the component also includes anterior and posterior chamfer portions, it can be desirable to shape the femur so that load is imposed primarily on the distal bone facing portion of the bone facing surfaces of the component when it is placed is under load after implantation. This can be achieved by shaping the femur so that, when the femoral component is slid on to the femur, contact is established between the distal face of the femur and the distal portion of the bone facing surface of the component before such contact between the femur and the chamfer portions. The contact between the distal face of the femur and the distal portion of the bone facing surface of the component effectively limits the movement of the femoral component on to the end of the femur.

BRIEF SUMMARY OF THE INVENTION

The present invention provides a femoral component in which rails are provided on one or more portions of its bone facing surface which define one or more recesses between them. For example, the rail and recess features can be provided on the anterior and posterior chamfer portions of the bone facing surface. The femur can then be prepared to receive the femoral component so that, when the distal portion of the bone facing surface of the component is in contact with the distal face of the femur, there is a space between the bases of the recesses on the component and the facing surfaces of the femur. In another arrangement, the rail and recess features can be provided on the distal portion of the bone facing surface. The femur can then be prepared to receive the femoral component so that, when the anterior and posterior chamfer portions of the bone facing surface of the component are in contact with the respective chamfer faces of the femur, there is a space between the base of the recess on the distal portion of the bone facing surface of the component and the facing surface of the femur.

Accordingly, the invention provides a femoral component of a knee joint prosthesis having a facing bearing surface for articulation with a tibial bearing surface and an opposite bone facing surface, in which the bone facing surface has:
  a. an anterior portion for engaging the femur on its anterior side,
  b. a posterior portion for engaging the femur on its posterior side,
  c. a distal portion for engaging the distal end face of the femur,
  d. an anterior chamfer portion located between the anterior portion and the distal portion, which is inclined to each of the anterior portion and the distal portion, and
  e. a posterior chamfer portion located between the posterior portion and the distal portion, which is inclined to each of the posterior portion and the distal portion,
  in which at least one of the anterior chamfer portion and the posterior chamfer portion of the bone facing surface has spaced apart medial and lateral rails with at least one recess between them.

The invention also provides a system for use in a surgical procedure on a patient's knee, which comprises:

a. a femoral component of a knee joint prosthesis having a bearing surface for articulation with a tibial bearing surface and an opposite bone facing surface, in which the bone facing surface has:
  i. an anterior portion for engaging the femur on its anterior side,
  ii. a posterior portion for engaging the femur on its posterior side,
  iii. a distal portion for engaging the distal end face of the femur,
  iv. an anterior chamfer portion located between the anterior portion and the distal portion, which is inclined to each of the anterior portion and the distal portion, and
  v. a posterior chamfer portion located between the posterior portion and the distal portion, which is inclined to each of the posterior portion and the distal portion, in which each of the distal, anterior and posterior portions of the bone facing surface is planar over at least part of its area, and b. a guide block having a planar distal surface which can be fastened to the distal face of a patient's femur on which the distal resection cut has been made to define the locations relative to the plane of the distal resection cut of planes on which the anterior and posterior chamfer cuts can be performed, in which the distance between (a) an anterior reference line extending parallel to the plane of the anterior chamfer cut and intersecting the plane of the distal surface at a point midway between the intersections between the planes of the distal surface and the anterior chamfer cuts and the planes of the distal surface and the posterior chamfer cuts and (b) the plane of the anterior chamfer cut is $G_{Ant}$, and the distance between (a) a posterior reference line extending parallel to the plane of the posterior chamfer cut and intersecting the plane of the distal surface at a point midway between the intersections between the planes of the distal surface and the anterior chamfer cuts and the planes of the distal surface and posterior chamfer cuts and (b) the plane of the posterior chamfer cut is $G_{Post}$, and in which:

(A) the anterior chamfer portion of the bone facing surface of the femoral component has spaced apart medial and lateral rails with at least one recess between them, with the distance between (a) an anterior implant reference line extending parallel to the anterior chamfer portion of the bone facing surface and intersecting the distal portion of the said surface at a point midway between the intersections between the distal portion and the anterior and posterior chamfer portions and (b) the tip edge of the rails being $I_{AntRail}$, and the distance between (a) the anterior implant reference line and (b) the base of the recess between the rails being $I_{AntRecess}$, the value of $(I_{AntRecess}-G_{Ant})$ being at least about 0.5 mm, and/or:

(B) the posterior chamfer portion of the bone facing surface of the femoral component has spaced apart medial and lateral rails with at least one recess between them, with the distance between (a) a posterior implant reference line extending parallel to the posterior chamfer portion of the bone facing surface and intersecting the distal portion of the said surface at a point midway between the intersections between the distal portion and the anterior and posterior chamfer portions and (b) the tip edge of the rails being $I_{PostRail}$, and the distance between (a) the posterior implant reference line and (b) the base of the recess between the rails being $I_{PostRecess}$, the value of $(I_{PostRecess}-G_{Post})$ being at least about 0.5 mm.

The reference lines on the guide block extend in a plane which is perpendicular to the plane of the distal surface of the guide block and to the planes of the chamfer cuts. The reference lines on the femoral component extend in a plane which is perpendicular to the distal and chamfer portions of the bone facing surface of the femoral component.

Each of the distal, anterior and posterior portions of the bone facing surface will usually be planar over the majority of at least 70% of its area, for example at least about 85% of its area, or at least about 95% of its area.

Implantation of the femoral component of the invention can be performed in a procedure in which the distal femur is prepared to receive the femoral component in a sliding fit. The femur is prepared so that there is face-to-face contact between the femur and the femoral component on the anterior, distal and posterior portions of its bone facing surface. The femur is prepared so that there is clearance between the femur and the bases of the recesses in one or more of the chamfer portions of its bone facing surface. The clearance between the femur and the bases of the or each recess in the chamfer portions should preferably be such that the rails provided along the edges of each recess contact the femur when there is face-to-face contact between the femur and the femoral component on the anterior, distal and posterior portions of its bone facing surface.

The provision of recesses on at least one of the anterior and posterior chamfer portions of the bone facing surface of the femoral component can help to ensure that load is imposed on the distal bone facing portion of the bone facing surfaces of the component when it is placed is under load after implantation with a lower load placed on the or each chamfer portion of the bone facing surface in which one or more recesses are provided.

It can be preferred that medial and lateral rails are provided on each of the anterior and posterior chamfer portions of the bone facing surface of the femoral component. This can help to ensure that load is imposed on the distal bone facing portion of the bone facing surfaces of the component when it is placed is under load after implantation with a lower load on the chamfer portions of the bone facing surface.

The invention also provides a system for use in a surgical procedure on a patient's knee, which comprises:

a. a femoral component of a knee joint prosthesis having a bearing surface for articulation with a tibial bearing surface and an opposite bone facing surface, in which the bone facing surface has:
  i. an anterior portion for engaging the femur on its anterior side,
  ii. a posterior portion for engaging the femur on its posterior side,
  iii. a distal portion for engaging the distal end face of the femur,
  iv. an anterior chamfer portion located between the anterior portion and the distal portion, which is inclined to each of the anterior portion and the distal portion, and v. a posterior chamfer portion located between the posterior portion and the distal portion, which is inclined to each of the posterior portion and the distal portion, in which each of the anterior, anterior chamfer, posterior chamfer and posterior portions of the bone facing surface is planar over at least part of its area, and the distal portion of the bone facing surface has spaced apart medial and lateral rails with at least one recess between them, b. a guide block having a planar distal surface which can be fastened to the distal face of a patient's femur on which the distal resection cut has been made to define the locations relative to the plane of the distal resection cut of planes on which the anterior and posterior chamfer cuts can be performed, the guide block defining a guide block reference line at the intersection of the planes of the anterior and posterior cuts so that the distance between the reference line and the planar distal surface is $G_{Dist}$, and in which the distal portion of the bone facing surface of the femoral component has spaced apart medial and lateral rails with at least one recess between them, with the distance between (a) an implant reference line lying at the intersection of the planes of the anterior chamfer and posterior chamfer portions of the bone facing surface and (b) the tip edge of the rails being $I_{DistRail}$, and the distance between (a) the implant reference line and (b) the base of the recess between the rails being $I_{DistRecess}$, the value of $(G_{Dist} - I_{DistRecess})$ being at least about 0.5 mm.

The reference lines on the guide block extend in a plane which is perpendicular to the plane of the distal surface of the guide block and to the planes of the chamfer cuts. The reference line on the femoral component is defined by the intersection of two planes.

Each of the anterior, anterior chamfer, posterior chamfer and posterior portions of the bone facing surface will usually be planar over the majority of at least 70% of its area, for example at least about 85% of its area, or at least about 95% of its area.

Implantation of the femoral component of the invention can be performed in a procedure in which the distal femur is prepared to receive the femoral component in a sliding fit. The femur is prepared so that there is face-to-face contact between the femur and the femoral component on the anterior, anterior chamfer, posterior chamfer and posterior portions of its bone facing surface. The femur is prepared so that there is clearance between the femur and the base of the or each recess in the distal portion of its bone facing surface. The clearance between the femur and the base of the or each recess should preferably be such that the rails provided along the edges of each recess contact the femur when there is face-to-face contact between the femur and the femoral component on the anterior, anterior chamfer, posterior chamfer and posterior portions of its bone facing surface.

The provision of recesses on at least one of the distal portion of the bone facing surface of the femoral component can help to ensure that load is imposed on the anterior and posterior chamfer bone facing portions of the bone facing surfaces of the component when it is placed is under load after implantation with a lower load on the distal portion of the bone facing surface in which one or more recesses are provided.

A number of features of the invention are applicable whether the recess and rail features are provided on the distal portion of the bone facing surface of the femoral component or on one or both of the chamfer portions.

It will often be preferred that the medial rail is located at the medial edge of the femoral component and the lateral rail is located at the lateral edge of the femoral component. The rails will then be continuations of the medial and lateral side walls of the femoral component.

Contact between the rails and the facing surface portions of the prepared femur means that no gap is visible to the surgeon between the femur and one or each of the relevant portions of the bone facing surface of the femoral component when inspecting the fit between the femur and the femoral component, even when the load that is carried by the portions of the femoral component having the recess and rails (either one or both of the chamfer portions, or the distal portion) is small or zero (less than that carried by either the distal portion, or one or both of the chamfer portions, respectively). This feature can enable the invention to deliver significant advantages. For example, the absence of a gap between the femur and all of the bone facing surface of the femoral component can help to reduce the likelihood of material being admitted to space between the femur and the femoral component. It can also provide the surgeon with greater confidence that the femur has been shaped appropriately for fitting the femoral component. Contact between the rails and the femur can also facilitate ingrowth of bone tissue which interacts with the femoral component on the rails to contribute to fixing the component in place, without that bone tissue having to span a gap between the component and the bone.

The ability of rails on one or both of the chamfer portions or on the distal portion of the femoral component to penetrate the prepared femur depends on factors such as the width of the rails, the shape of the rails, the length of the rails, the number of rails and so on. It can be preferred that the width of each rail at its bone facing edge is not more than about 4 mm, more preferably not more than about 3 mm, for example not more than about 2 mm. It can be preferred that each rail is tapered inwardly towards its bone facing edge. For example, it can be tapered inwardly so that its width at its bone facing edge is not more than about 1.5 mm or not more than about 1 mm. When a rail is tapered inwardly towards its bone facing edge, its width at its base can be at least about 2 mm, for example at least about 3 mm, or at least about 4 mm.

The depth of the recess which is provided between the medial and lateral rails can be at least about 0.5 mm, optionally at least about 1.0 mm, or at least about 1.5 mm. The depth of the recess will frequently be not more than about 3.5 mm, optionally not more than about 2.5 mm. The depth of the recess is equal to the value of $(I_{AntRecess} - I_{AntRail})$ in the case of a recess on the anterior chamfer portion of the bone facing surface, $(I_{PostRecess} - I_{PostRail})$ in the case of a recess on the posterior chamfer portion, and $(I_{DistRail} - I_{DistRecess})$ in the case of a recess on the distal portion.

It can be preferred that, when the medial and lateral rails are provided on the anterior chamfer portion of the bone facing surface, they extend from the distal portion to the anterior portion. It can be preferred that, when the medial and lateral rails are provided on the posterior chamfer portion of the bone facing surface, they extend from the distal portion to the posterior portion. Rails that extend continuously from the distal portion to the anterior or posterior portion (as the case may be) can provide continuous contact between the femoral component and the femur along the entire lengths of the medial and lateral edges of the femoral component. This can help to prevent ingress of material into the space between the component and the femur.

It can be preferred that, when the medial and lateral rails are provided on the distal portion of the bone facing surface, they extend from the anterior chamfer portion to the posterior chamfer portion. Rails that extend continuously from the anterior chamfer portion to the posterior chamfer portion can provide continuous contact between the femoral component and the femur along the entire lengths of the medial and lateral edges of the femoral component. This can help to prevent ingress of material into the space between the component and the femur.

The femoral component can include at least one additional rail located between the medial and lateral rails. Medial and lateral rails which are provided at the medial and lateral edges of the femoral component can extend along the edges of the femoral component and can so be aligned with those edges, extending between the anterior end of the femoral component and the posterior end of the femoral component. When such rails penetrate the surface of the prepared femur, they can help to locate the component on the femur against movement relative to the femur, especially in a direction which is aligned with the medial-lateral axis.

The provision of the medial and lateral rails, and one or more optional additional rails, can also contribute to fixation of the femoral component to the femur by increasing the contact area between the femoral component and the prepared surface of the femur, in particular compared with a femoral component which is designed so that, when implanted, there is little or no contact between the femoral component and the femur in the chamfer regions. The increased contact area provides for increased fixation through bone ingrowth.

Medial and lateral rails which are provided at the medial and lateral edges of the femoral component extend along the edges of the femoral component and so will be curved to follow those edges, while extending generally between the anterior end of the femoral component and the posterior end of the femoral component.

At least one additional rail can be included which is generally aligned with the medial and lateral rails and extends at least part of the distance between the anterior and posterior edges of one or more of the recesses. A rail which is generally aligned with the medial and lateral rails need not be exactly parallel to either of those rails but will extend generally along the anterior-posterior direction. A rail which is spaced apart from the medial and lateral edges of the femoral component can be arranged so that it is straight and extends generally in the anterior-posterior direction.

In the case of a femoral component of a total knee prosthesis, the posterior chamfer portions of the bone facing surface are generally provided on the separate medial and lateral condyle limbs of the femoral component, separated by a gap which corresponds to the intercondylar fossa in the natural knee. It is preferred that the posterior chamfer portions on each of the condylar limbs has spaced apart medial and lateral rails with at least one recess between them.

A gap between separate medial and lateral condyle limbs of the femoral component in the posterior and posterior chamfer portions of the component can extend at least partially across the distal portion of the component towards the anterior chamfer portion. Accordingly, each condyle of a total knee prosthesis will generally have posterior, posterior chamfer and distal portions at least of its bone facing surface.

A femoral component of a unicondylar knee prosthesis has just one condylar limb with a posterior chamfer portion of the bone facing surface of the component. The posterior chamfer portion of the bone facing surface can have spaced apart medial and lateral rails with at least one recess between them.

It can be appropriate in some circumstances for the anterior chamfer portion of the bone facing surface of the femoral component to have a central rib which will be in the sulcus region of the component. This can be appropriate when the femoral component is of a total knee prosthesis. The rib can be seen as a form of rail. The rib can be wider than rails provided at the medial and lateral edges of the anterior chamfer portion. A central rib can provide reinforcement for the component against forces imposed on it when in use, in particular reinforcing the component in the sulcus region. It can be necessary to remove bone tissue in the anterior chamfer region of the femur to accommodate a central rib on the anterior chamfer portion of the bone facing surface of the femoral component. It is also envisaged that the anterior chamfer portion of the bone facing surface could have a recess which extends continuously across the width of the chamfer portion between ribs at or close to the medial and lateral edges, without a central rib and without any additional rails.

At least one additional rail can be included which extends across a recess between the medial and lateral rails, generally transverse to the medial and lateral rails, for example extending part or all of the distance between the medial rail to the lateral rail.

When the posterior chamfer portion of the bone facing surface of the component has spaced apart medial and lateral rails with at least one recess between them, it can be preferred that the proportion of the area of the posterior chamfer portion of the bone facing surface that is provided by the recess (or recesses) is at least about 50%, more preferably at least about 60%, especially at least about 65%, for example at least about 75%.

When the anterior chamfer portion of the bone facing surface of the component has spaced apart medial and lateral rails with at least one recess between them, it can be preferred that the proportion of the area of the anterior chamfer portion of the bone facing surface (disregarding the area of a central rib if present in the sulcus region of the component) that is provided by the recess (or recesses) is at least about 50%, more preferably at least about 60%, especially at least about 65%, for example at least about 75%.

When the distal portion of the bone facing surface of the component has spaced apart medial and lateral rails with at least one recess between them, it can be preferred that the proportion of the area of the distal portion of the bone facing surface (disregarding other features such as pegs which extend into the femoral condyles) that is provided by the recess (or recesses) is at least about 50%, more preferably at least about 60%, especially at least about 65%, for example at least about 75%.

It can be preferred in some femoral components that the distance between the anterior and posterior portions of the bone facing surface of the femoral component, measured parallel to the anterior-posterior axis, is at least as great at the proximal end of the posterior condyle as at the distal end of the posterior condyle. In this way, the anterior and posterior portions of the bone facing surface can be arranged so that they are parallel to one another or so that they diverge in a direction away from the distal portion of the bone facing surface. If the angle between the anterior and posterior portions of the bone facing surface will frequently be not more than about 5°. This can facilitate fitting the femoral component on to a prepared femur.

The distal portion of the bone facing surface can be arranged so that it is approximately perpendicular to the direction in which the femoral component is moved relative to the femur when it is fitted on to a prepared femur. When the anterior and posterior portions of the bone facing surface of the component are planar and parallel to one another, it can be appropriate for the distal portion of the bone facing surface to be perpendicular to the planes of each of the anterior and posterior portions. When the anterior and posterior portions of the bone facing surface of the component diverge, it can be appropriate for the angle between the distal portion and the anterior portion to be equal to the angle between the distal portion and the posterior portion.

The distal portion of the bone facing surface can be provided with at least one peg, for example two pegs, which extend from the bone facing surface perpendicularly thereto, to be received in corresponding drilled bores in the distal face of the femur. The peg or pegs can be tapered inwardly towards their free ends.

The femoral component of the invention is intended to be fixed in place relative to a patient's femur without the use of a bone cement so that it is fixed by an interaction between the bone facing surface of the component and the surface of the bone with which that surface is in contact when the femoral component is in place. Accordingly, when the recess and rail features are provided on one or both of the chamfer portions of the bone facing surface, it can be preferred that each of the other portions (anterior, distal and posterior, and sometimes one of the chamfer portions) of the bone facing surface is planar from edge to edge (disregarding any protrusions on the surface which might be intended to be received in appropriate bores or other cavities which are provided in the surface of the bone). For example, each of the planar portions of the bone facing surface can be characterised by not having a rail at any of its edges which might inhibit the formation of close surface to surface contact between the bone facing surface of the component and the adjacent bone surfaces. The femur can be prepared for contacting such a component with corresponding planar surfaces. Planar bone surfaces can be easier for a surgeon to create accurately during surgery than surfaces which are not planar.

When the recess and rail features are provided on one or both of the chamfer portions of the bone facing surface, it can be preferred that each of the anterior, distal and posterior portions of the bone facing surface is adapted to promote fixation to bone without the use of a bone cement. When the recess and rail features are provided on the distal portion of the bone facing surface, it can be preferred that each of the anterior, anterior chamfer, posterior chamfer and posterior portions of the bone facing surface is adapted to promote fixation to bone without the use of a bone cement. The bone facing surface can be so adapted by provision of a porous structure into which bone tissue can grow. The bone facing surface can be so adapted by provision of a coating of a material which promotes interaction with bone tissue, for example a coating of a hydroxyapatite material.

The femoral component can be made from metallic materials that are commonly used in the manufacture of joint prosthesis components. Examples include cobalt-chromium based alloys (including alloys of cobalt, chromium and molybdenum), titanium and titanium based alloys, and certain stainless steels.

The femoral component can be made in a range of sizes so that an appropriate component can be selected by a surgeon that is appropriate having regard to the size of the patient's femur.

The femoral component can be provided together with other components of a knee prosthesis. For example, it can be provided with a tibial component. The tibial component can be provided with a bearing component. When a bearing component is provided, it can be made from a material which is different from that of the femoral and tibial components, such as a polymeric material (especially ultrahigh molecular weight polyethylene) or a ceramic material. Such combinations of components are known.

It is important that a patient's femur is prepared accurately to receive the femoral component of the invention, in particular as to the locations of the anterior, distal, posterior, anterior chamfer and posterior chamfer surfaces (which frequently will be planar surfaces). Instruments which can be used to locate the positions of the surfaces relative to anatomic features, frequently with reference to pre-operative images of the patient's bones, are well known and can be used to locate the surfaces on a femur which is to be prepared to receive the femoral component of the invention. It is understood that the precise location of each of the bone cuts relative to the other bone cuts, and angular relationship between the cuts, should be appropriate for the selected femoral component. These relationships can be determined using an appropriate cutting block which is positioned on the distal face of the femur after the distal cut has been made to form the distal face of the prepared femur. An example of a suitable cutting block is a 4-in-1 cutting block which can be used to locate the planes of each of the anterior, posterior, anterior chamfer and posterior chamfer cuts. It includes surfaces which can be used to guide a saw blade during each of those cutting steps. An example of a 4-in-1 cutting block is disclosed in EP-A-2774554.

More than one cutting block might be used to locate the planes of each of the anterior, posterior, anterior chamfer and posterior chamfer cuts. For example, a first cutting block might be used to guide the anterior and posterior cuts and a second cutting block might be used to guide the chamfer cuts. An example of a cutting block which can be used to guide the chamfer cuts is disclosed in EP-A-2671523.

In order to prepare the femur to receive a femoral component with clearance between the bone and the femoral component in one more portions of the interface between the two (distal portion or one or both of the anterior and posterior chamfer portions) as provided by the invention, the cutting block which is used to guide a blade when performing the bone cuts will position the blade to provide clearance between the resection plane defined by the cut bone and the base of the recess in the distal or one or both of the chamfer portions of the bone facing surface of the component. Preferably, the clearance should be such that the rails which define the or each recess are in contact with the cut bone on the or each chamfer surface of the bone.

Optionally, when rails are provided on the anterior chamfer portion of the bone facing surface, the value of ($G_{Ant}-I_{AntRail}$) can be at least about 0.05 mm, or at least about 0.2 mm, or at least about 0.5 mm, or at least about 1 mm, or at least about 1.5 mm, or at least about 2 mm, and possibly 3 mm or more. This is a measure of the depth to which the rails become embedded in the anterior chamfer surface of the prepared femur when the component is seated on the femur with the distal portion of the bone facing surface of the femoral component firmly engaging the distal surface of the prepared femur.

Optionally, when rails are provided on the posterior chamfer portion of the bone facing surface, the value of ($G_{Post}-I_{PostRail}$) can be at least about 0.05 mm, or at least about 0.2 mm, or at least about 0.5 mm, or at least about 1 mm, or at least about 1.5 mm, or at least about 2 mm, and possibly 3 mm or more. This is a measure of the depth to which the rails become embedded in the posterior chamfer surface of the prepared femur when the component is seated on the femur with the distal portion of the bone facing surface of the femoral component firmly engaging the distal surface of the prepared femur.

Optionally, when rails are provided on the distal portion of the bone facing surface, the value of ($I_{DistRail}$–$G_{Dist}$) can be at least about 0.05 mm, or at least about 0.2 mm, or at least about 0.5 mm, or at least about 1 mm, or at least about 1.5 mm, or at least about 2 mm, and possibly 3 mm or more. This is a measure of the depth to which the rails become embedded in the distal surface of the prepared femur when the component is seated on the femur with the anterior and posterior chamfer portions of the bone facing surface of the femoral component firmly engaging the anterior and posterior chamfer surface of the prepared femur.

Optionally, when rails are provided on the anterior chamfer portion of the bone facing surface, the value of ($I_{AntRecess}$–$G_{Ant}$) can be at least about 1.0 mm, or at least about 1.5 mm, or at least about 2.0 mm, or at least about 2.5 mm. This is a measure of the depth of the space between the anterior chamfer surface of the prepared femur and the anterior chamfer portion of the bone facing surface of the femoral component, when the component is seated on the femur with the distal portion of the bone facing surface of the femoral component firmly engaging the distal surface of the prepared femur (frequently with the rails on the anterior chamfer portion embedded in the anterior chamfer surface of the bone).

Optionally, when rails are provided on the posterior chamfer portion of the bone facing surface, the value of ($I_{PostRecess}$–$G_{Post}$) can be at least about 1.0 mm, or at least about 1.5 mm, or at least about 2.0 mm, or at least about 2.5 mm. This is a measure of the depth of the space between the posterior chamfer surface of the prepared femur and the posterior chamfer portion of the bone facing surface of the femoral component, when the component is seated on the femur with the distal portion of the bone facing surface of the femoral component firmly engaging the distal surface of the prepared femur (frequently with the rails on the posterior chamfer portion embedded in the posterior chamfer surface of the bone).

Optionally, when rails are provided on the distal portion of the bone facing surface, the value of ($G_{Dist}$–$I_{DistRecess}$) can be at least about 1.0 mm, or at least about 1.5 mm, or at least about 2.0 mm, or at least about 2.5 mm. This is a measure of the depth of the space between the distal surface of the prepared femur and the distal portion of the bone facing surface of the femoral component, when the component is seated on the femur with the anterior and posterior chamfer portions of the bone facing surface of the femoral component firmly engaging the anterior and posterior surfaces of the prepared femur (frequently with the rails on the distal portion embedded in the distal surface of the bone).

A femoral component will frequently have separate medial and lateral condyles, separated by a gap or notch which corresponds to the intercondylar fossa in the natural knee. Each condyle will have posterior, posterior chamfer and distal portions at least of its bone facing surface.

DETAILED DESCRIPTION OF THE INVENTION

Figure 1:
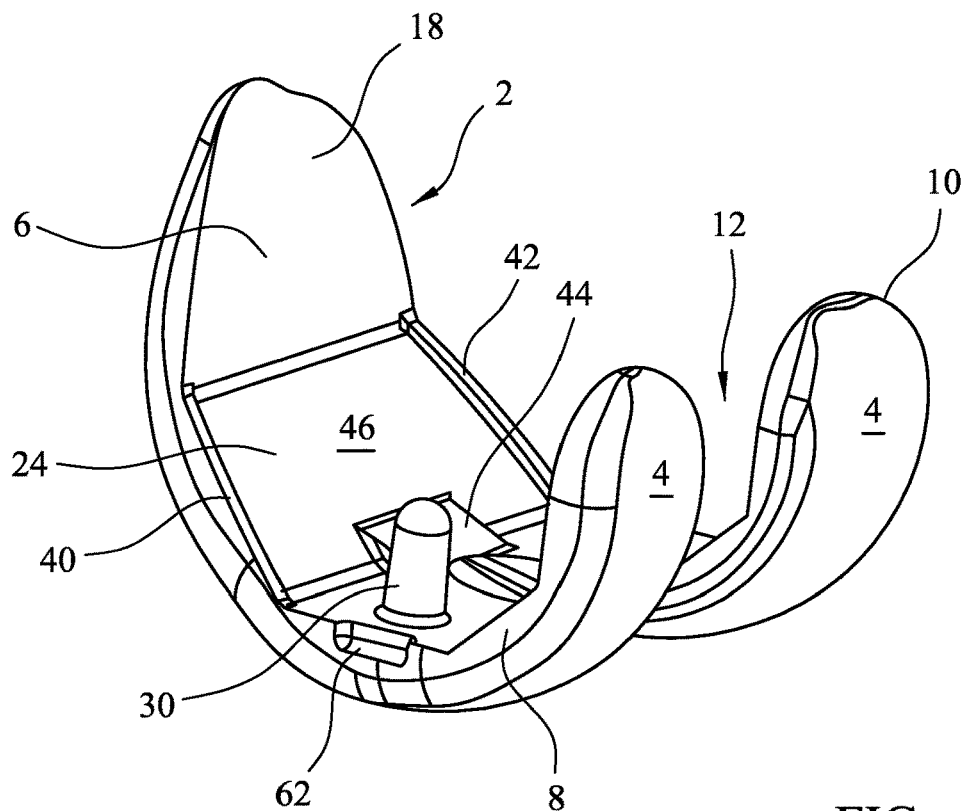
FIGS. 1 and 2 are isometric views of a femoral component showing the anterior and anterior chamfer portions, and the posterior and posterior chamfer portions, respectively of the bone facing surface of the component.
Figure 2:
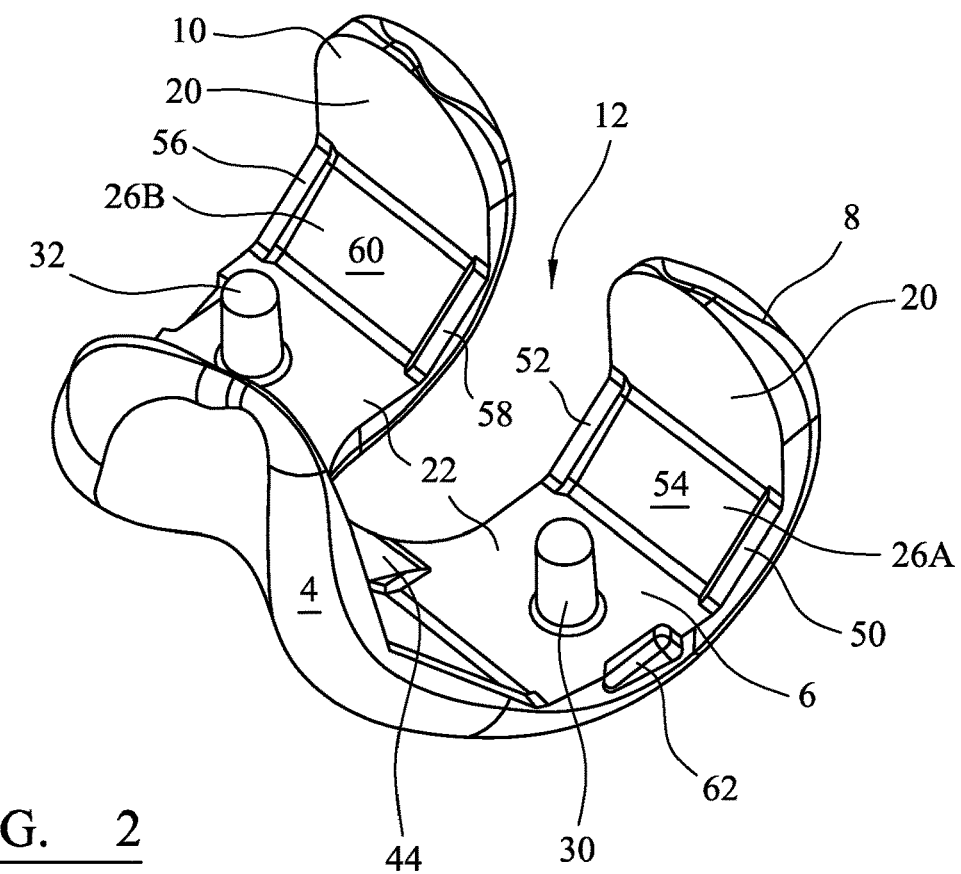

Referring to the drawings, FIGS. 1 and 2 show a femoral component 2 of a total knee prosthesis which is suitable for implantation in a patient's left knee. The component has a bearing surface 4 for articulation with a tibial bearing surface and an opposite bone facing surface 6. The bearing surface is highly polished to provide low friction articulation. The provision of highly polished bearing surfaces on orthopaedic joint prosthesis components is well known. For some applications, it might be appropriate for the bone facing surface to be provided with a coating of a hydroxyapatite material. The provision of such coatings on the bone facing surfaces of implant components which are intended for implantation without use of a bone cement is well known.

The femoral component has lateral and medial condylar limbs 8, 10 posteriorly, which are separated by a gap 12 which corresponds to the intercondylar fossa in the natural knee. The gap can accommodate the cruciate ligaments.

The bone facing surface 6 has an anterior portion 18 for engaging the femur on its anterior side, a posterior portion 20 for engaging the femur on its posterior side, and a distal portion 22 for engaging the distal end face of the femur.

The bone facing surface 6 has an anterior chamfer portion 24 located between the anterior portion 8 and the distal portion 22, which is inclined to each of the anterior portion and the distal portion. It also has a posterior chamfer portion 26 located between the posterior portion 20 and the distal portion 22, which is inclined to each of the posterior portion and the distal portion.

The gap 12 between the lateral and medial condylar limbs 8, 10 extends across the distal portion of the component towards the anterior chamfer portion.

Each of the anterior portion 8, the posterior portion 20, the distal portion 22, the anterior chamfer portion 24 and the posterior chamfer portion 26 is planar. It will frequently be preferable that the planes of the anterior and posterior portions diverge from one another. For example, the angle between the plane of the anterior portion and a plane which is parallel to the distal portion is about 5°. For example, the angle between the plane of the posterior portion and a plane which is parallel to the distal portion is about 1°. The angle between the anterior chamfer portion and the distal portion is about 48°. The angle between the posterior chamfer portion and the distal portion is about 44.5°.

The distal portion 22 of the bone facing surface 6 has lateral and medial pegs 30, 32 extending perpendicularly from it. The pegs are tapered inwardly towards their free ends which are rounded.

As can be seen in FIG. 1, the anterior chamfer portion 24 of the bone facing surface 6 of the component has a lateral rail 40 at its lateral edge and a medial rail 42 at its medial edge. It has a central rib 44 in the sulcus region whose width is slightly greater than that of the gap 12 between the lateral and medial condylar limbs 8, 10. A recess 46 is located between the lateral rail 40 and the medial rail 42. A short central rib 44 is provided at the anterior end of the gap 12 between the lateral and medial condyles. The rib bridges the distal and anterior chamfer portions 22, 24 of the bone facing surface of the component.

As can be seen in FIG. 2, the bone facing surface 6 of the component includes a posterior chamfer portion 26A, 26B on each of the lateral and medial condylar limbs 8, 10. The posterior chamfer portion 26A on the lateral condylar limb 8 has a lateral rail 50 at its lateral edge and an opposite rail 52. A lateral recess 54 is located between the lateral rail 50 and the opposite rail 52. The posterior chamfer portion 26B on the medial condylar limb 10 has a medial rail 56 at its medial edge and an opposite rail 58. A medial recess 60 is located between the medial rail 56 and the opposite rail 58.

Each of the rails mentioned above has a width of 2 mm. The depth of the recesses is 0.5 mm.

The proportion of the area of the posterior chamfer portion 26 of the bone facing surface 6 that is provided by the recesses 54, 60 is at least about 60%, for example about 64% in one embodiment or about 84% in another embodiment.

The proportion of the area of the anterior chamfer portion 24 of the bone facing surface 6 that is provided by the recess 46 is at least about 90%.

The femoral component has notches 62 on the distal portion 22 of the bone facing surface 6 which can receive the tips of an instrument which can be used to grip the component so that it can be manipulated for implantation on a patient's femur. An example of a femoral component implantation instrument which can be used in this way is disclosed in WO-A-2012/001385.

Figure 3:
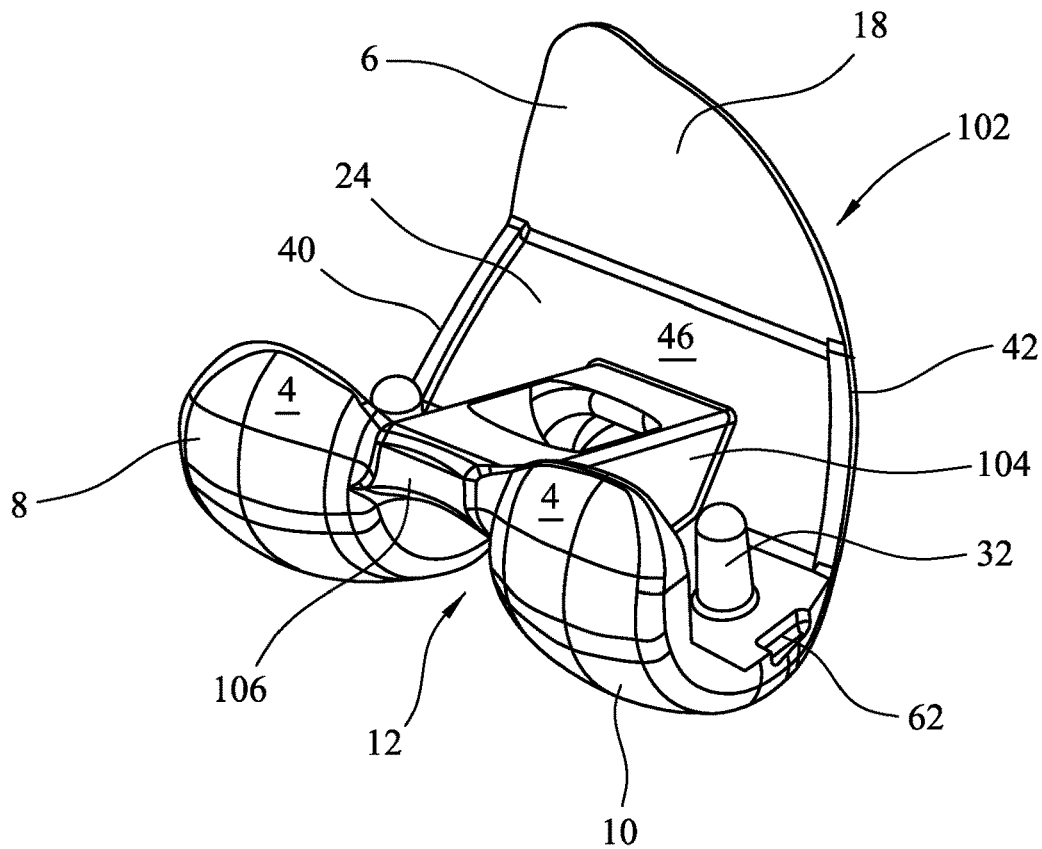
FIGS. 3 and 4 are isometric views of another femoral component showing the anterior and anterior chamfer portions, and the posterior and posterior chamfer portions, respectively of the bone facing surface of the component.
Figure 4:
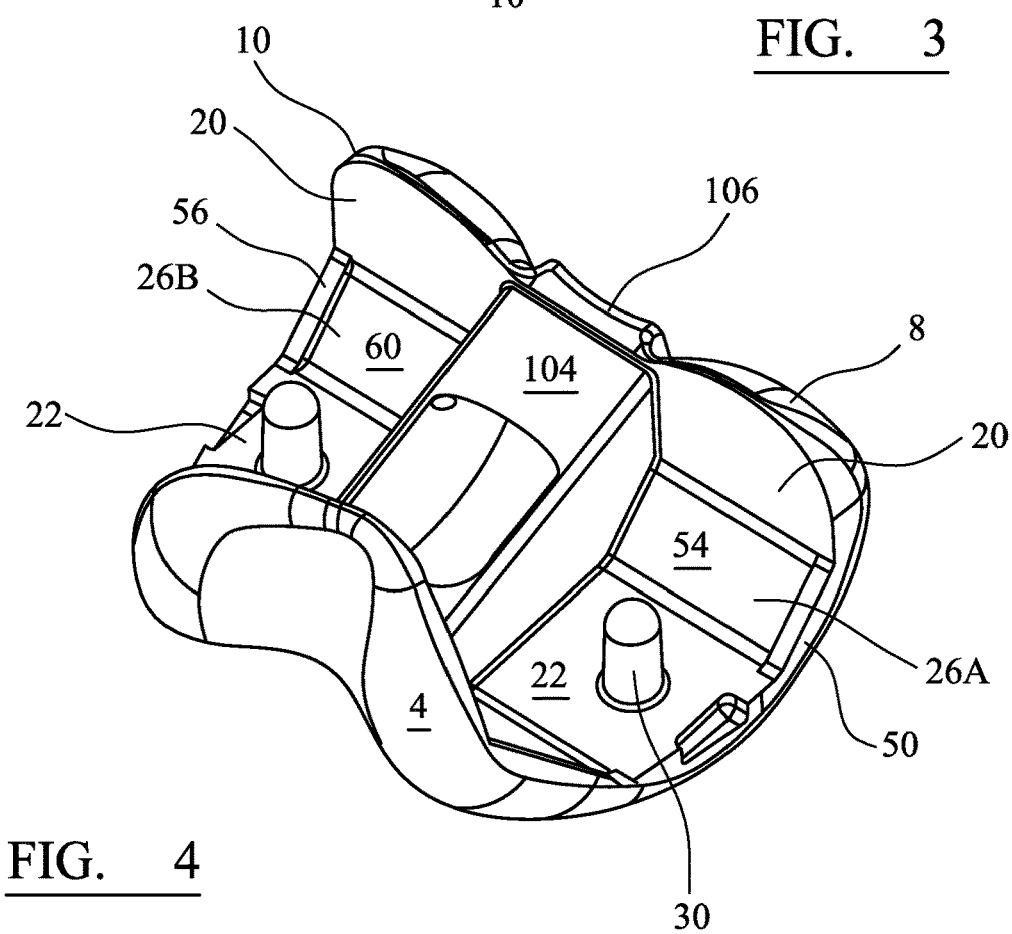

FIGS. 3 and 4 show a femoral component 102 which has features in common with the component which is shown in FIGS. 1 and 2. The same reference numerals are used in FIGS. 3 and 4 to denote those features.

The femoral component 102 shown in FIGS. 3 and 4 is configured for implantation in a circumstance in which a patient's posterior cruciate ligament has been sacrificed. The knee joint is stabilised against translation of the femur posteriorly relative to the tibia when the knee is extended by means of a post on the tibia (generally provided on a bearing component on the tibia (not shown)) which is engaged by a cam on the femoral component. Accordingly, the femoral component 102 shown in FIGS. 3 and 4 has a box structure 104 provided in the space between the lateral and medial condyles 8, 10, in the gap between the condyles. A cam 106 is provided at the posterior edge of the box structure which engages a post on a tibial component when the knee is extended.

In the femoral component 102 shown in FIGS. 3 and 4, the box structure 104 can be seen to extend from the posterior end of the gap 12 between the condyles, through the posterior, posterior chamfer and distal portions 20, 26, 22 of the bone facing surface 6 of the component, on to the anterior chamfer portion 24 in the central region between the lateral and medial edges.

The box structure 104 also defines the medial extent of the posterior chamfer portion 26A on the lateral condylar limb 8, which therefore extends the lateral rail 50 and the box structure. The box structure 104 also defines the lateral extent of the posterior chamfer portion 26B on the medial condylar limb 10, which therefore extends between the medial rail 56 and the box structure.

Figure 5:
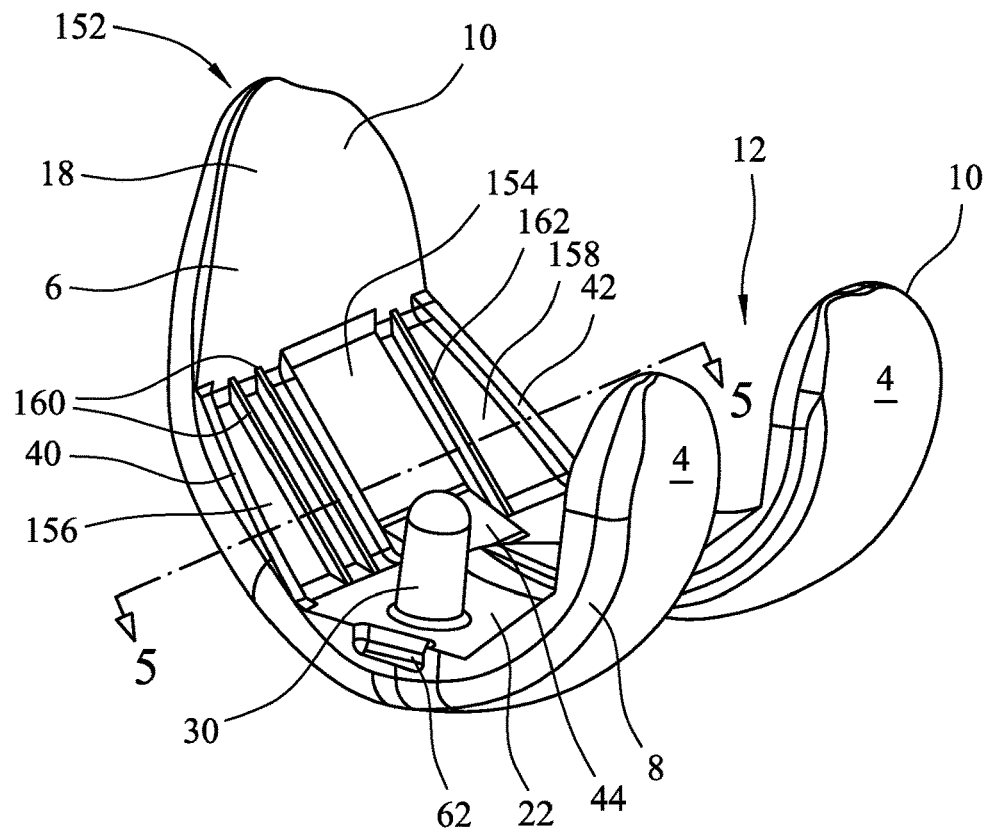
FIGS. 5 and 6 are isometric views of a further femoral component showing the anterior and anterior chamfer portions, and the posterior and posterior chamfer portions, respectively of the bone facing surface of the component.
Figure 6:
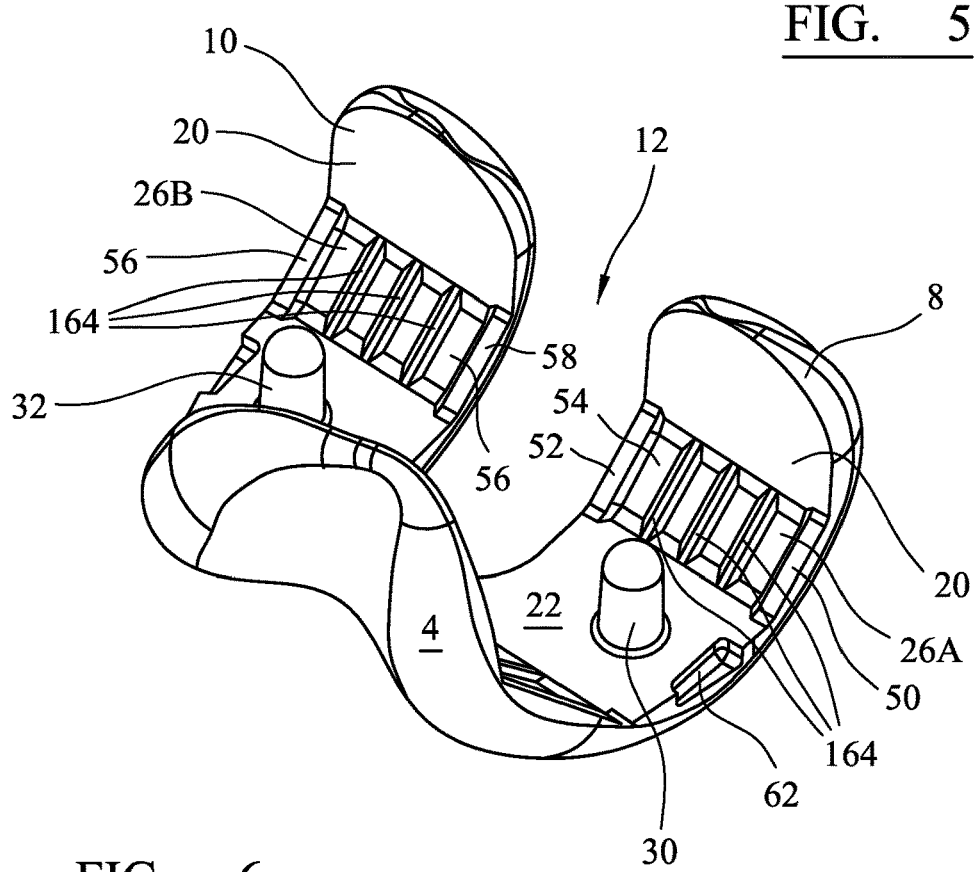

FIGS. 5 and 6 show a femoral component 152 which has features in common with the component which is shown in FIGS. 1 and 2. The same reference numerals are used in FIGS. 5 and 6 to denote those features.

The femoral component shown in FIGS. 5 and 6 differs from that shown in FIGS. 1 and 2 in that it has a central rib 154 extending in the anterior posterior direction across the anterior chamfer portion 24 of the bone facing surface 6. The rib is located in the sulcus region and has a width which is slightly greater than that of the gap 12 between the lateral and medial condylar limbs 8, 10. A lateral recess 156 is located between the lateral rail 40 and the central rib 154. A medial recess 158 is located between the medial rail 42 and the central rib 154. The central rib 154 can help to reinforce the anterior chamfer portion of the femoral component in the sulcus region.

Two additional rails 160 extend across the lateral recess 156 in the anterior chamfer portion 24 of the bone facing surface 6. A further additional rail 162 extends across the lateral recess 158. The additional rails are straight. They are generally aligned with the medial and lateral edges of the femoral component and are spaced apart from the medial and lateral edges so that they extend in a generally anterior-posterior direction. Each of the additional rails is tapered inwardly in the direction away from the base of the recess in which it is located towards the top edge of the rail so that the rail is narrower at its top edge than at its base. This can facilitate penetration of the surface of the prepared femur by the additional rails.

The femoral component 160 shown in FIGS. 5 and 6 has three additional rails 164 extending across each of the recesses 54, 60 in the lateral and medial posterior chamfer portions 26A, 26B of the bone facing surface 6. The additional rails are straight. They are generally aligned with the medial and lateral edges of the femoral component and are spaced apart from the medial and lateral edges so that they extend in a generally anterior-posterior direction. As in the anterior chamfer portion, the additional rails which extend across the recesses 54, 60 in the posterior chamfer portions are tapered inwardly towards their top edges.

The proportion of the area of the anterior chamfer portion 24 of the bone facing surface 6 that is provided by the recesses 156, 158 is at least about 60%, for example about 63%.

Figure 7:
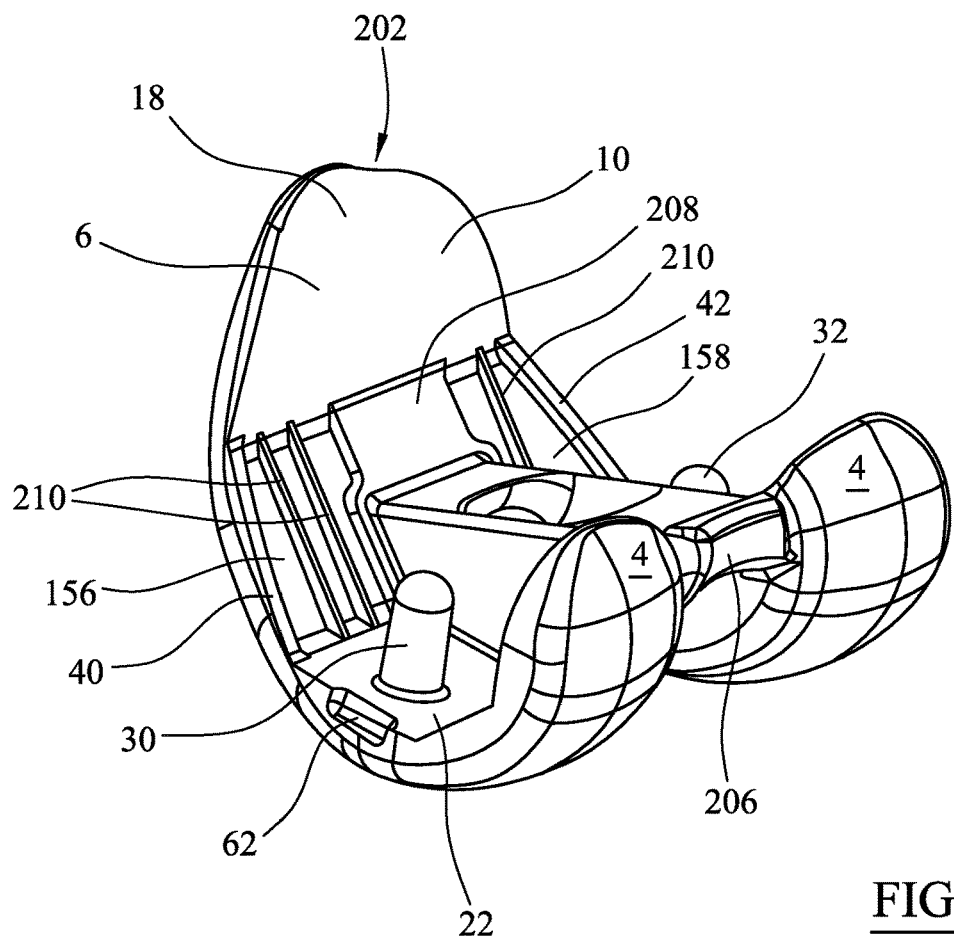
FIGS. 7 and 8 are isometric views of yet another femoral component showing the anterior and anterior chamfer portions, and the posterior and posterior chamfer portions, respectively of the bone facing surface of the component.
Figure 8:
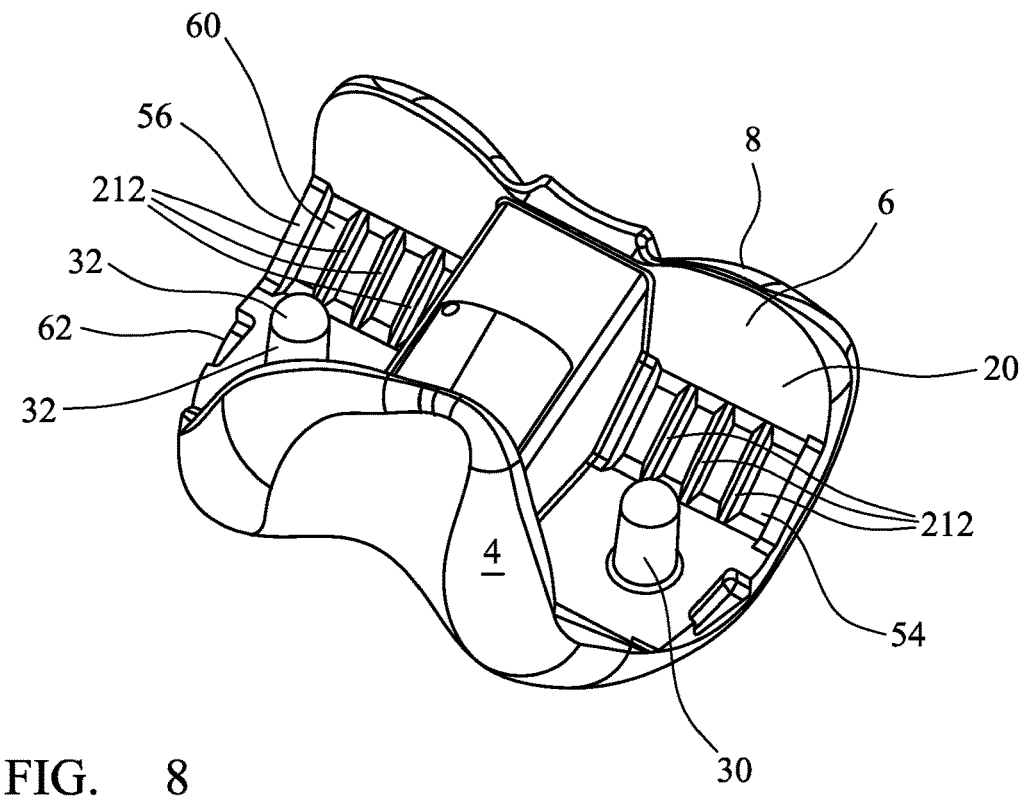

FIGS. 7 and 8 show a femoral component 202 which has features in common with the component which is shown in FIGS. 1 and 2. The same reference numerals are used in FIGS. 7 and 8 to denote those features.

The femoral component shown in FIGS. 7 and 8 is a posterior stabilised (PS) femoral component 202 having a box structure 204 provided in the space between the lateral and medial condyles 8, 10, in the gap between the condyles. A cam 206 is provided at the posterior edge of the box structure, which engages a post on an appropriate tibial component when the knee is extended. These features are present in the femoral component 102 which is described above with reference to FIGS. 3 and 4.

The femoral component shown in FIGS. 7 and 8 also has central rib 208, additional rails 210 extending across the lateral and medial recesses 156, 158 in the anterior chamfer portion 24 of the bone facing surface 6, and additional rails 212 extending across each of the recesses 54, 60 in the lateral and medial posterior chamfer portions 26A, 26B of the bone facing surface 6. The central rib and additional rails have features which are discussed above in relation to the femoral component shown in FIGS. 5 and 6.

Figure 9:
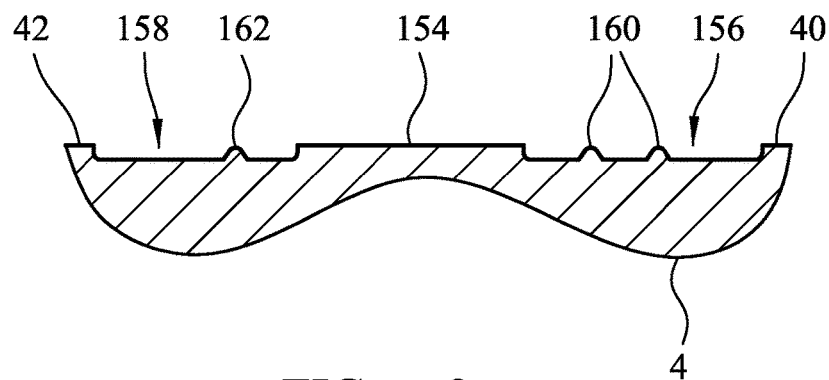
FIG. 9 is a cross section view of the femoral component shown in FIGS. 5 and 6 on the line S-S in FIG. 5.

FIG. 9 is a cross section view of the femoral component shown in FIGS. 5 and 6 taken through the anterior chamfer portion of the component on the line S-S in FIG. 5. The recesses that are provided in the chamfer portions are visible in the cross section view. It is intended that the femur should be prepared so that the anterior and posterior chamfer surfaces of the femur are positioned so that the bases of the recesses are spaced apart from the chamfer surfaces of the femur with the top edges of the rails 40, 42 and of the additional ribs 160, 162 in contact with the chamfer surfaces, when the bone contacting surfaces on the anterior, distal and posterior portions of the component are in close engagement with the corresponding surfaces of the femur.

A cutting block can be positioned against the distal face of the femur to perform the anterior, posterior, and anterior and posterior chamfer cuts. It includes surfaces which can be used to guide a saw blade during each of those cutting steps. It is recognised however that more than one cutting block might be used to perform these cuts. For example, a first cutting block might be used to guide the anterior and posterior cuts and a second cutting block might be used to guide the chamfer cuts.

In order to prepare the femur to receive a femoral component as provided by the invention, the cutting block which is used to guide a blade when performing one or each of the anterior and posterior chamfer cuts will position the blade to provide clearance between the resection plane defined by the cut bone on the chamfer surface(s) of the bone and the base of the recess in one or each of the chamfer portions of the bone facing surface of the component. Preferably, the clearance should be such that the rails which define the or each recess are in contact with the cut bone on the or each chamfer surface of the bone.

Figure 10:
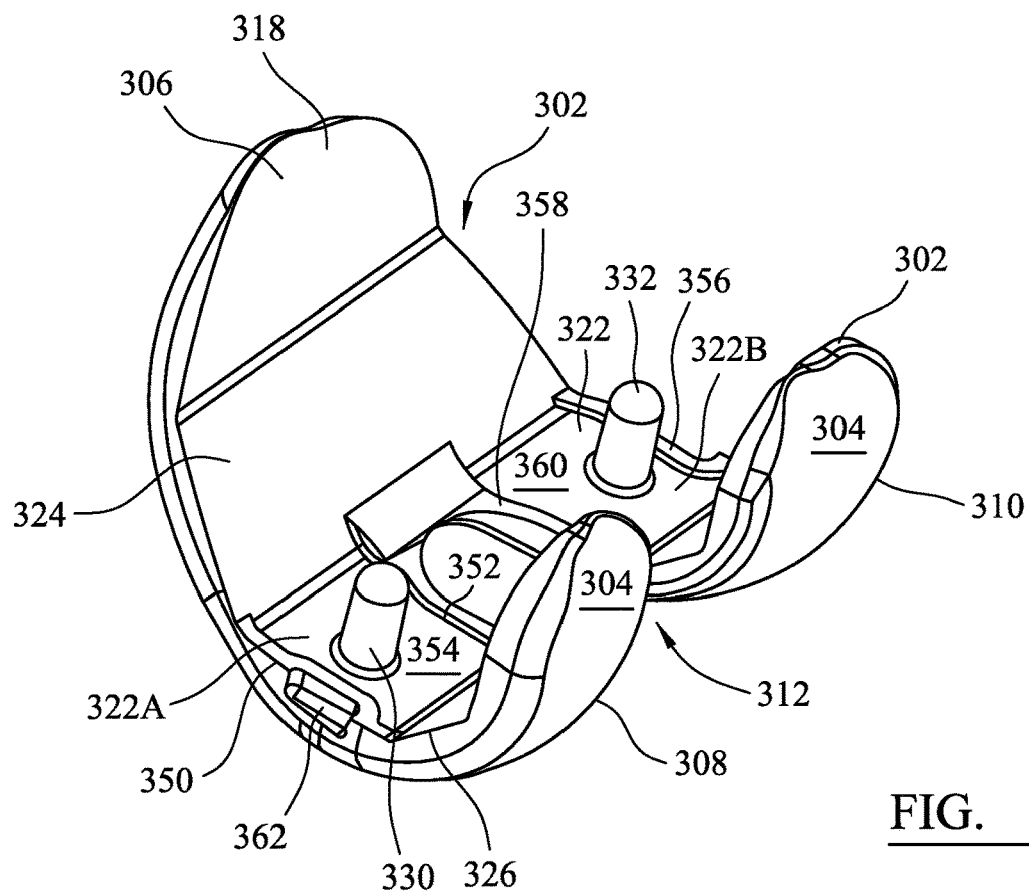
FIGS. 10 and 11 are isometric views of a femoral component showing the anterior, anterior chamfer and distal portions, and the posterior, posterior chamfer and distal portions, respectively of the bone facing surface of the component.
Figure 11:
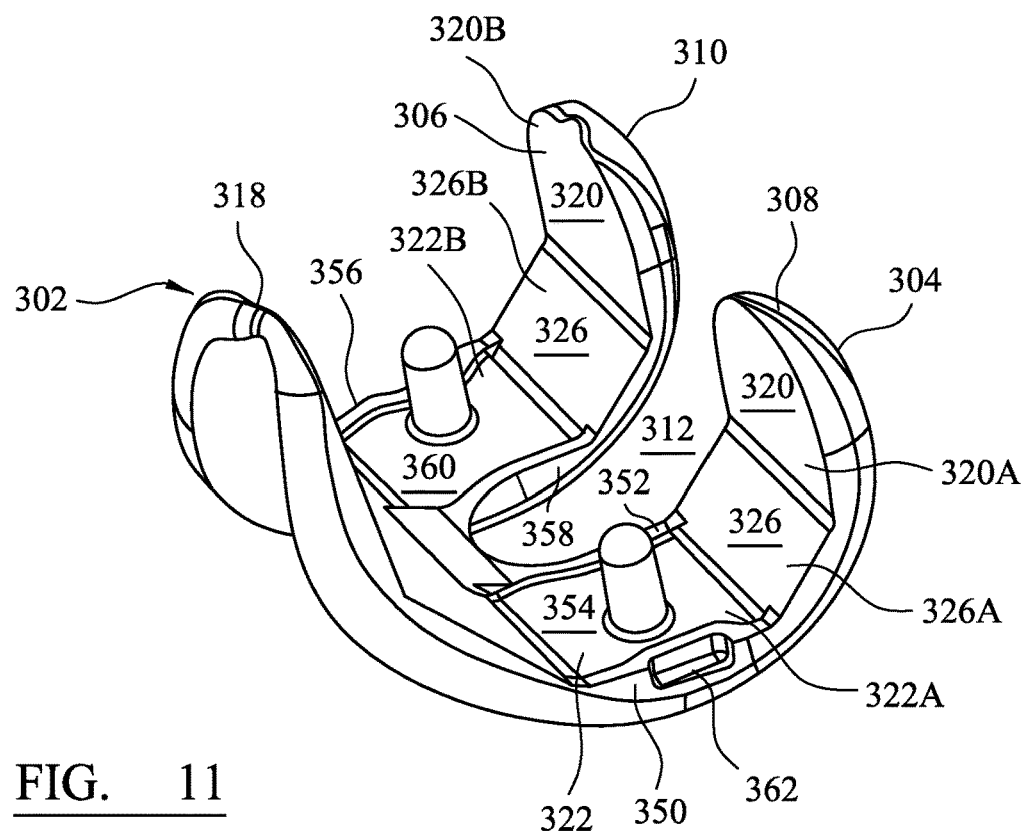

FIGS. 10 and 11 show a femoral component 302 of a total knee prosthesis which is suitable for implantation in a patient's left knee. The component has a bearing surface 304 for articulation with a tibial bearing surface and an opposite bone facing surface 306. The bearing surface is highly polished to provide low friction articulation. The provision of highly polished bearing surfaces on orthopaedic joint prosthesis components is well known. For some applications, it might be appropriate for the bone facing surface to be provided with a coating of a hydroxyapatite material. The provision of such coatings on the bone facing surfaces of implant components which are intended for implantation without use of a bone cement is well known.

The femoral component has lateral and medial condylar limbs 308, 310 posteriorly, which are separated by a gap 312 which corresponds to the intercondylar fossa in the natural knee. The gap can accommodate the cruciate ligaments.

The bone facing surface 306 has an anterior portion 318 for engaging the femur on its anterior side, a posterior portion 320 for engaging the femur on its posterior side, and a distal portion 322 for engaging the distal end face of the femur.

The bone facing surface 306 has an anterior chamfer portion 324 located between the anterior portion 318 and the distal portion 322, which is inclined to each of the anterior portion and the distal portion. It also has a posterior chamfer portion 326 located between the posterior portion 320 and the distal portion 322, which is inclined to each of the posterior portion and the distal portion.

The gap 312 between the lateral and medial condylar limbs 308, 310 extends partially across the distal portion of the component towards the anterior chamfer portion.

Each of the anterior portion 318, the posterior portion 320, the distal portion 322, the anterior chamfer portion 324 and the posterior chamfer portion 326 is planar. It will frequently be preferable that the planes of the anterior and posterior portions diverge from one another. For example, the angle between the plane of the anterior portion and a plane which is parallel to the distal portion is about 5°. For example, the angle between the plane of the posterior portion and a plane which is parallel to the distal portion is about 1°. The angle between the anterior chamfer portion and the distal portion is about 48°. The angle between the posterior chamfer portion and the distal portion is about 44.5°.

The bone facing surface 306 of the component includes a distal portion 322A, 322B, a posterior chamfer portion 326A, 326B, and a posterior portion 320A, 320B on each of the lateral and medial condylar limbs 308, 310.

The distal portion 322 of the bone facing surface 306 has lateral and medial pegs 330, 332 extending perpendicularly from it. The pegs are tapered inwardly towards their free ends which are rounded.

As can be seen in FIGS. 10 and 11, the distal portion 322A on the lateral condylar limb 308 has a lateral rail 350 at its lateral edge and an opposite rail 352. A lateral recess 354 is located between the lateral rail 350 and the opposite rail 352. The distal portion 322B on the medial condylar limb 310 has a medial rail 356 at its medial edge and an opposite rail 358. A medial recess 360 is located between the medial rail 356 and the opposite rail 358.

Each of the rails mentioned above has a width of 2 mm. The depth of the recesses is 0.5 mm.

The proportion of the area of the distal portions 322A, 322B of the bone facing surface 306 that is provided by the recesses 354, 360 is at least about 90%.

The femoral component has notches 362 on the distal portion 322 of the bone facing surface 306 which can receive the tips of an instrument which can be used to grip the component so that it can be manipulated for implantation on a patient's femur.

FIGS. 12 to 15 show a 4-in-1 cutting guide block 512 for use in the surgical preparation of the patient's distal femur during a knee replacement procedure. This and other guide blocks for use in the surgical preparation of a patient's femur during a knee replacement procedure are disclosed in EP-A-2774554 and are examples of guide blocks which can be used in the system of the present invention. As discussed below, a 4-in-1 cutting block 512 is used to perform four cuts on the patient's distal femur with the same block. The cuts are an anterior cut, a posterior cut, and two chamfer cuts.

The 4-in-1 cutting block 512 may be formed from polymeric materials such as, for example, polyamide, poly (phenylsulphone), or polyketone. The surfaces used to guide surgical instruments, such as cutting guide surfaces for guiding bone saws and bushings for guiding drills and surgical pins, are formed from a metallic material such as, for example, a steel, a titanium alloy, or a cobalt chromium alloy. Such use of metallic components or "inserts" prevents the surgical tools from coming into contact with the polymeric materials of the block's body.

The metallic components described herein may be secured to the polymer 4-in-1 cutting block in a number of different ways. For example, the metallic components may be over-moulded to the polymer cutting block or otherwise secured to it as part of the moulding process of the block. The metallic components may also be welded to the cutting block or secured to it with an adhesive. Other methods of securing the metallic components may also be employed.

The 4-in-1 cutting block 512 includes an outer surface 520 and a bone-engaging surface 522 positioned opposite the outer surface 520. The 4-in-1 cutting block 512 has an anterior cutting slot 524 formed near its anterior end 526. The anterior cutting slot 524 is an elongated slot extending in the medial/lateral direction. The anterior cutting slot 524 extends through the entire thickness of the 4-in-1 cutting block 512. The anterior cutting slot 524 therefore extends from the cutting block's outer surface 520 to its bone-engaging surface 522 and so is open to both surfaces. A metallic anterior cutting guide 528 is secured within the anterior cutting slot 524 of the polymer 4-in-1 cutting block 512. The anterior cutting guide 528 lines the anterior cutting slot 524 and is embodied as a captured cutting guide (i.e., it is closed on all sides so as to capture a saw blade therein), although the cutting block 512 and the cutting guide 528 may alternatively be embodied as a non-captured cutting guide. The anterior cutting guide 528 is sized and shaped to receive the blade (see FIG. 15) of a surgical saw or other cutting instrument and orient the blade to resect the anterior surface of the patient's femur during an orthopaedic surgical procedure.

The 4-in-1 cutting block 512 has a posterior cutting surface 530 formed near its posterior end 532. The posterior cutting surface 530 is an elongated surface extending in the medial/lateral direction. The posterior cutting surface 530 extends the entire thickness of the 4-in-1 cutting block 512. The posterior cutting surface therefore extends from the cutting block's outer surface 520 to its bone-engaging surface 522. A metallic posterior cutting guide 534 is secured to the posterior cutting surface 530 of the polymer 4-in-1 cutting block 512. The posterior cutting guide 534 is sized and shaped to support and guide the blade (see FIG. 15) of a surgical saw or other cutting instrument and orient the blade to resect the posterior surface of the patient's femur during an orthopaedic surgical procedure. The posterior cutting guide 534 shown in the drawing is a non-captured cutting guide. Features of this cutting guide could be incorporated in a captured cutting guide.

The 4-in-1 cutting block 512 has a chamfer cutting slot 536 formed near its middle. Specifically, the chamfer cutting slot 536 is located posteriorly of the anterior cutting slot 524 and anteriorly of the posterior cutting surface 530. The chamfer cutting slot 536 is an elongated slot extending in the medial/lateral direction. The chamfer cutting slot 536 extends through the entire thickness of the 4-in-1 cutting block 512. The slot therefore extends from the cutting block's outer surface 520 to its bone-engaging surface 522 and, as a result, is open to both surfaces. The chamfer cutting slot 536 is defined by a sidewall 538 of the 4-in-1 cutting block that includes an anterior edge 540 extending in the medial/lateral direction and a posterior edge 542 that is spaced apart from the anterior edge 540 and likewise extends in the medial/lateral direction. The chamfer cutting slot 536 has enlarged rounded medial and lateral ends. In particular the medial edge 544 of the sidewall 538 defining the chamfer cutting slot 536 is cylindrical in shape (i.e., circular when viewed in the front elevation of FIG. 13) and has a diameter that is larger than the A/P width of the slot 536 (i.e., the distance between anterior edge 540 and the posterior edge 542 of the sidewall 538). On the opposite end of the chamfer cutting slot 536, the lateral edge 546 of the sidewall 538 is identical in shape and size. Accordingly, in the device shown in the drawings, the chamber cutting slot 536 takes on the form of two cylinders spaced at opposite medial and lateral ends connected by a elongated planar slot.

Figure 12:
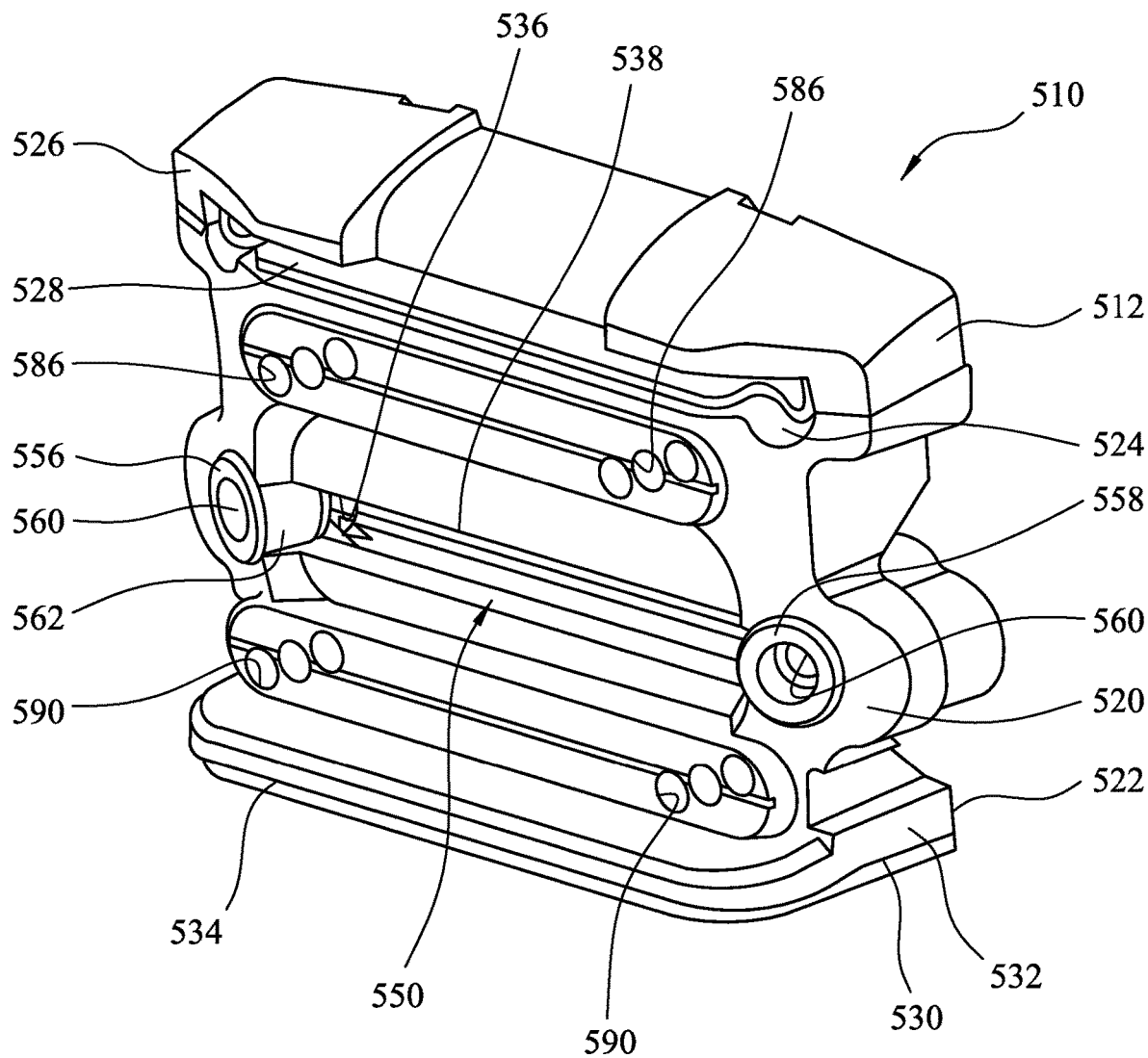
FIG. 12 is an isometric view of a cutting block.
Figure 13:
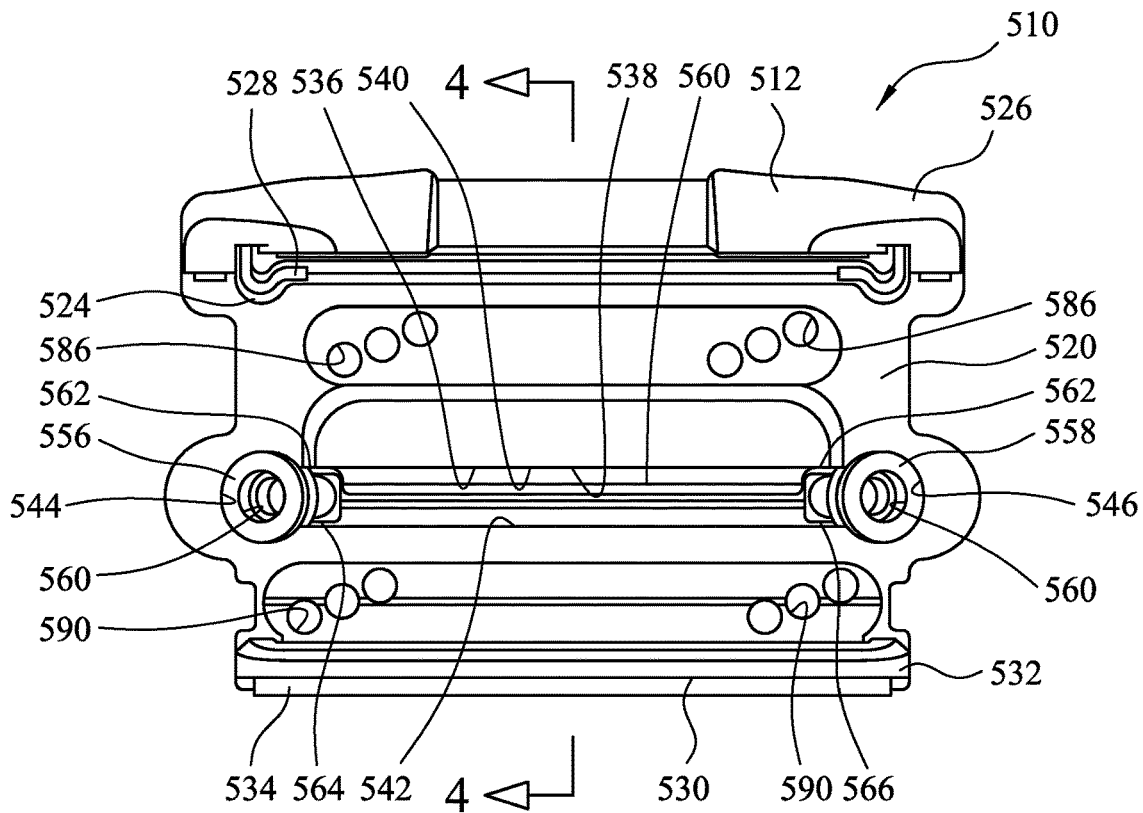
FIG. 13 is an elevation view showing the outer surface of the cutting block of FIG. 12.
Figure 14:
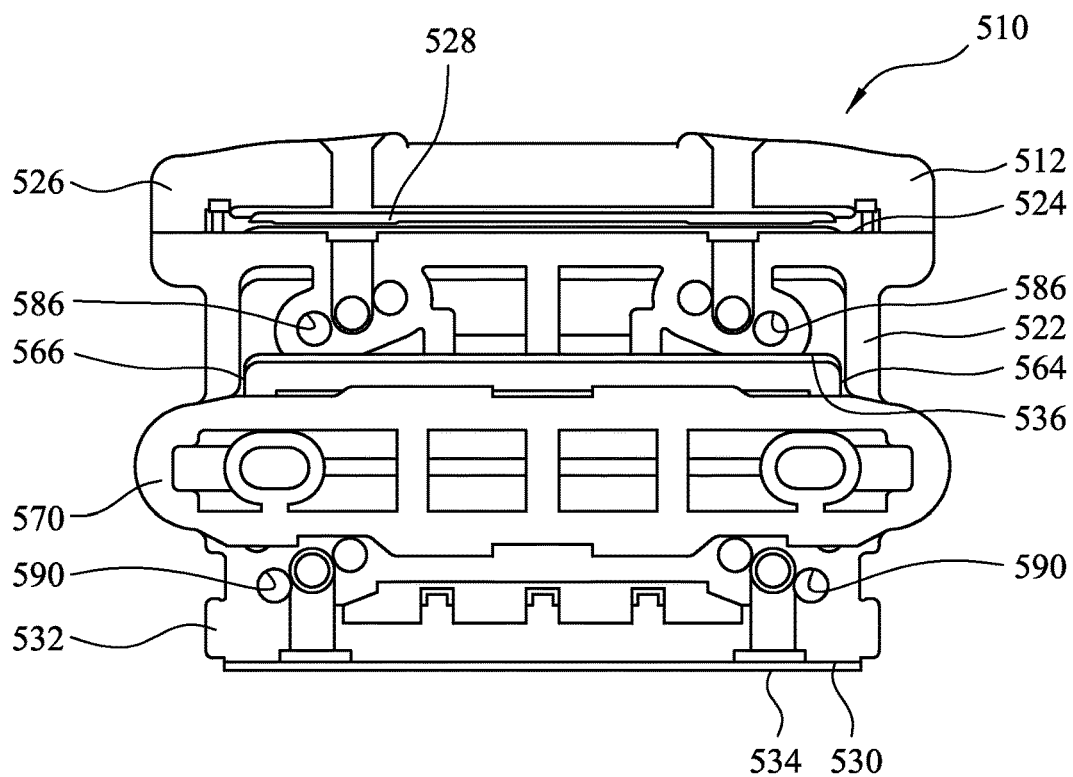
FIG. 14 is a front elevation view showing the bone-engaging surface of the cutting block of FIG. 12.
Figure 15:
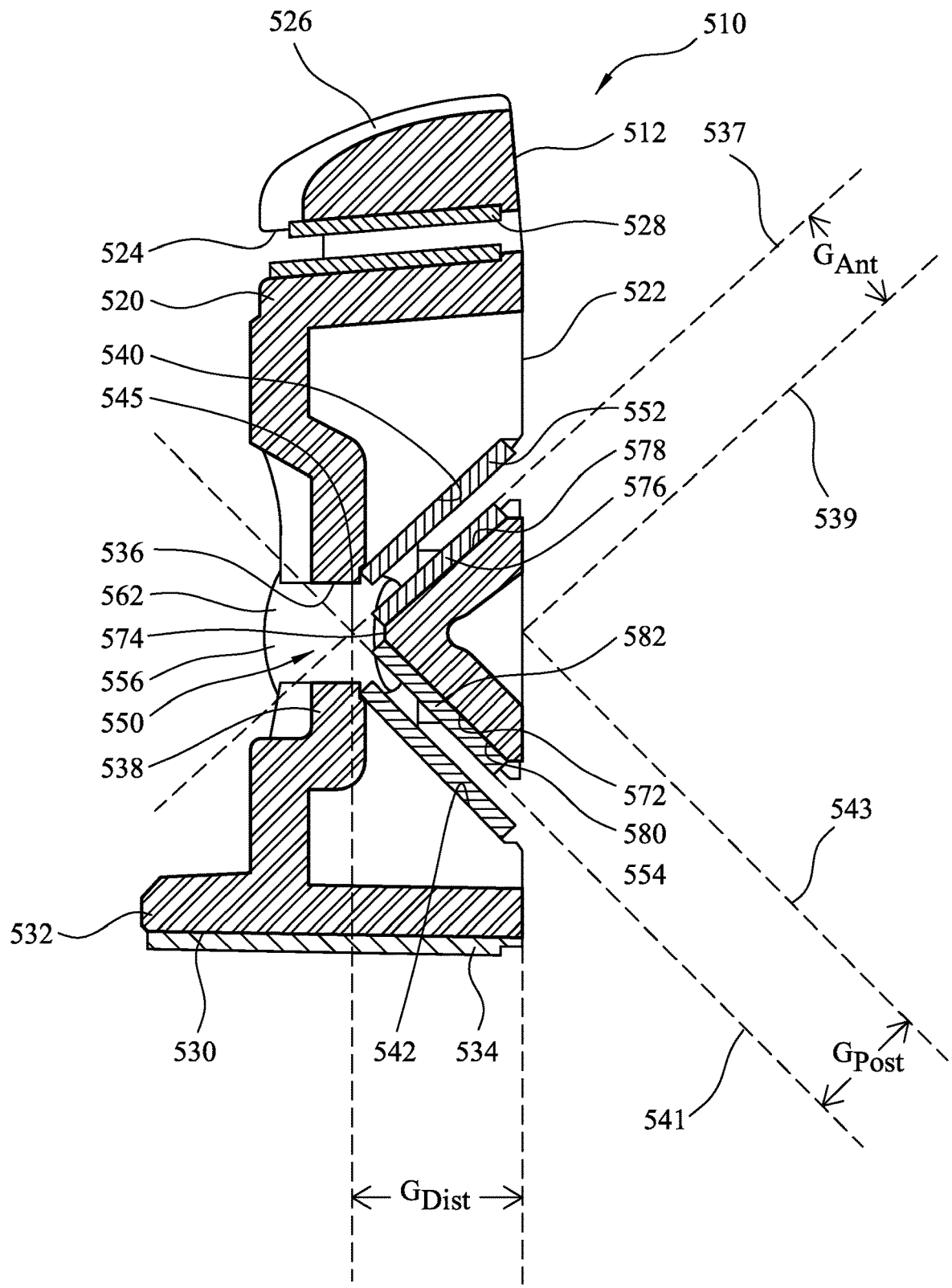
FIG. 15 is a sectional elevation view of the cutting block, taken along the line 4-4 identified in FIG. 13, as viewed in the direction of the arrows.

As shown in FIGS. 12, 13 and 15, a metallic captured chamfer cutting guide assembly 550 is positioned in the chamfer cutting slot 536. The assembly 550 includes a metallic planar cutting guide 552 secured to the anterior edge 540 of the sidewall 538 defining the anterior side of the chamfer cutting slot 536, along with a metallic planar cutting guide 554 secured to the posterior edge 542 of the sidewall 538 defining the posterior side of the chamfer cutting slot 536. As can be seen best in FIG. 15 the planar cutting guides 552, 554 are spaced apart from one another in the anterior/posterior direction and are arranged at an oblique angle relative to one another. The longitudinal axis of the planar cutting guides 552, 554 extends in the medial/lateral direction.

The medial and lateral ends of the captured chamfer cutting guide assembly 550 are defined by a pair of metallic bushings 556, 558. In particular, the metallic bushing 556 is positioned in the enlarged cylindrically-shaped medial end of the chamfer cutting slot 536. The metallic bushing 556 is therefore secured in contact with the medial edge 544 of the sidewall 538 defining the medial end of the chamfer cutting slot 536. The metallic bushing 558 is positioned in the enlarged cylindrically-shaped lateral end of the chamfer cutting slot 536. The metallic bushing 558 is therefore secured in contact with the lateral edge 546 of the sidewall 538 defining the lateral end of the chamfer cutting slot 536.

The metallic bushings 556, 558 are cylindrically-shaped and have an elongated bore 560 extending through them. The elongated bore 560 is sized to receive a fixation or guide pin for pinning the 4-in-1 cutting block to the patient's distal femur (see FIG. 18) and, optionally, a drill such that the patient's femur may be pre-drilled prior to installation of the guide pins if the surgeon so desires. The metallic bushings 556, 558 are identical in shape and include an annularly-shaped outer surface 562. As can be seen in FIG. 13, the outer surface 562 of the metallic bushing 556 is positioned at the medial end 564 of the planar cutting guides 552, 554, with the outer surface 562 of the metallic bushing 558 being positioned at the lateral end 566 of the planar cutting guides 552, 554. In the device shown in the drawings, the outer surface 562 of the metallic bushings 556, 558 is slightly spaced apart from the respective medial end 564 and lateral end 566 of the planar cutting guides 552, 554 (i.e., the bushings 556, 558 are not positioned in contact with the planar cutting guides 552, 554). Such spacing allows for capture of the blade of a bone saw, while also providing for relief from overly tight tolerances in the manufacturing process. However, it is also envisaged that the metallic bushings 556, 558 might be positioned in contact with the respective medial end 564 and lateral end 566 of the planar cutting guides 552, 554.

As can be seen best in FIGS. 12 and 15, the 4-in-1 cutting block 512 has a wedge component 570 secured to its bone-engaging surface 522. Like the 4-in-1 cutting block 512, the wedge component 570 is formed from polymeric materials. The wedge component 570 has a wedge-shaped cutting surface 572. The "leading" edge 574 of the wedge-shaped cutting surface 572 extends into the chamfer cutting slot 536. A metallic planar cutting guide 576 is secured to the anterior surface 578 of the wedge-shaped cutting surface 572, with a metallic planar cutting guide 580 being secured to the posterior surface 582 of the wedge-shaped cutting surface 572. Like the cutting guides 552, 554, the planar cutting guides 576, 580 are spaced apart from one another and are arranged at an oblique angle relative to one another. The longitudinal axis of the planar cutting guides 576, 580 extends in the medial/lateral direction. As can be seen in FIG. 15, the cutting guide 576 is spaced apart from, and parallel to, the cutting guide 552, with the cutting guide 580 being spaced apart from, and parallel to, the cutting guide 554. In such a way, the cutting guides 552, 576 cooperate to guide a saw blade during performance of the anterior chamfer cut, with the cutting guides 554, 580 cooperating to guide the saw blade during performance of the posterior chamfer cut (see FIG. 18).

Like the planar cutting guides 552, 554, the outer surface 562 of the metallic bushing 556 is positioned at the medial end of the planar cutting guides 576, 580, with the outer surface 562 of the metallic bushing 558 being positioned at the lateral end of the planar cutting guides 576, 580. In the device shown in the drawings, the outer surface 562 of the metallic bushings 556, 558 is slightly spaced apart from the respective medial end and lateral end of the planar cutting guides 576, 580 (i.e., the bushings 556, 558 are not positioned in contact with the planar cutting guides 576, 580). Such spacing allows for capture of the blade of a bone saw, while also providing for relief from overly tight tolerances in the manufacturing process. However, it is also envisaged that the metallic bushings 556, 558 are positioned in contact with the respective medial end and lateral end of the planar cutting guides 576, 580.

Figure 17:
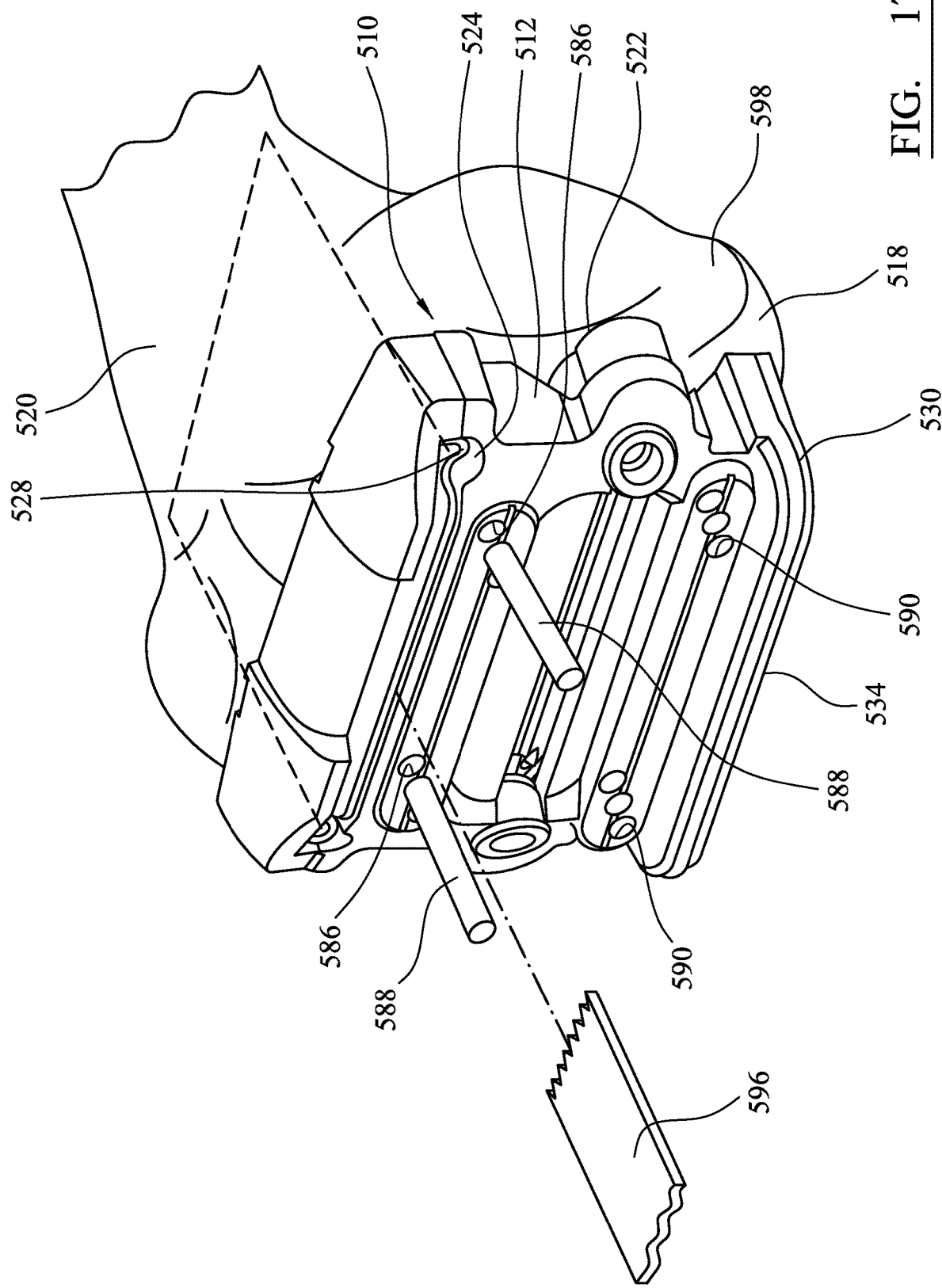
FIG. 17 is a view similar to FIG. 16, but showing the cutting block of FIG. 12 being used to perform the anterior and posterior cuts on the distal end of the patient's femur.

The 4-in-1 cutting block 512 has a plurality of guide holes 586 defined therein that are sized to receive a pair of fixation or guide pins 588 (see FIG. 17). The holes 586 are positioned between the anterior cutting slot 524 and the chamfer cutting slot 536 and extend between the outer surface 520 and the bone-engaging surface 522 of the cutting block 512. The holes 586 are arranged in a staggered pattern to permit the surgeon to change the position of the cutting block 512 on the patient's femur without having to remove the fixation pins 588, as described in greater detail below.

The 4-in-1 cutting block 512 also includes another plurality of guide holes 590 positioned between the chamfer cutting 536 and the posterior cutting surface 530. Each guide hole 590 is sized to receive one of the fixation pins 588 in a similar manner to the guide holes 586 and thereby extends between the outer surface 520 and the bone-engaging surface 522 of the cutting block 512. Like the guide holes 586, the guide holes 590 are arranged in a staggered pattern to permit the surgeon to change the position of the cutting block 512 on the patient's femur without having to remove the fixation pins 588.

In operation, the surgeon may use the orthopaedic surgical instrument 510 to prepare the distal end 518 of the patient's femur 100 to receive a prosthetic femoral component. To do so, the surgeon may secure the 4-in-1 cutting block 512 to the patient's femur 100 and then use the metallic cutting guides of the cutting block 512 to guide a cutting saw blade in making a series of four resections of the distal end 518 of the femur.

Figure 16:
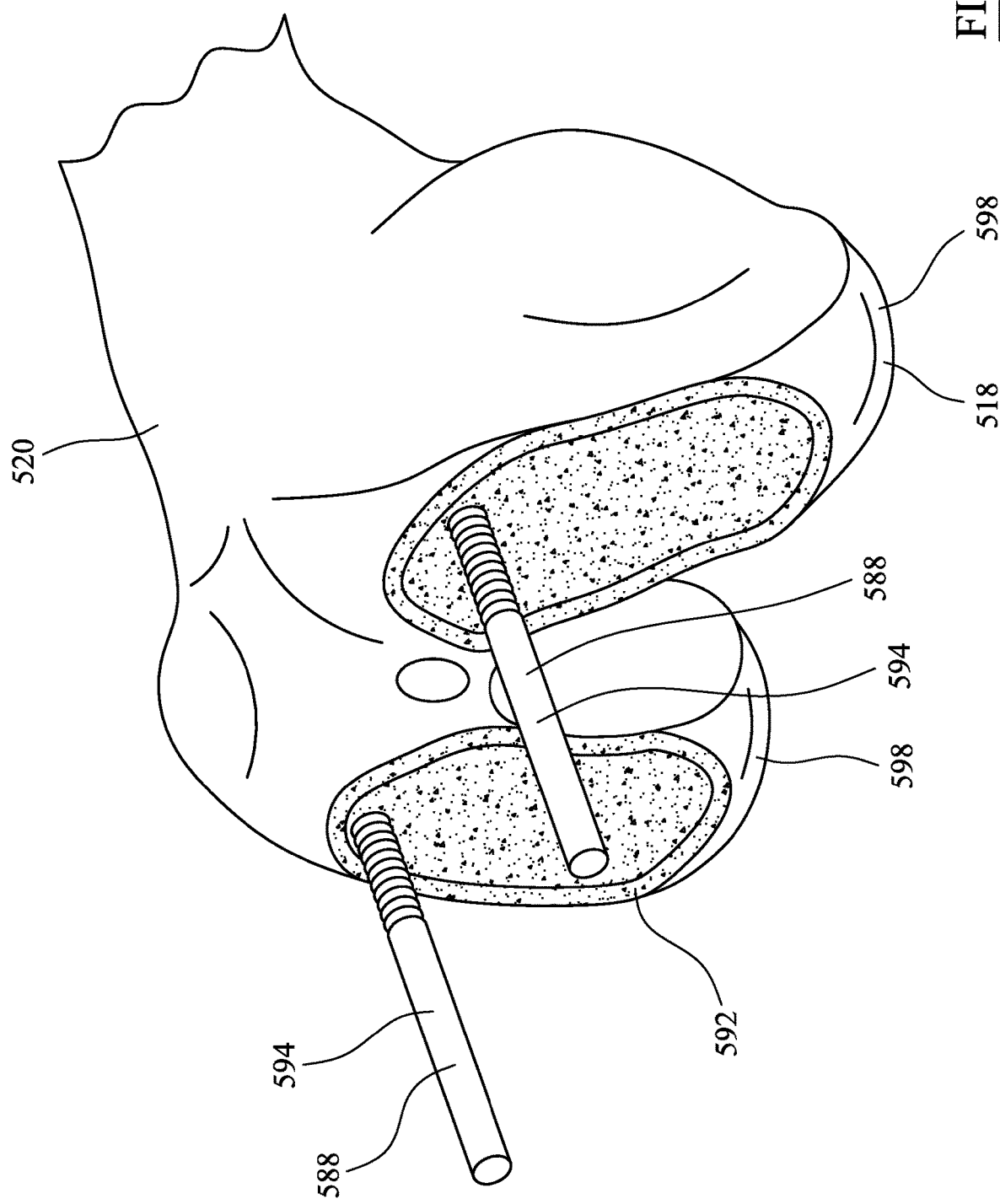
FIG. 16 is an isometric view of the distal end of a patient's femur with a pair of fixation pins secured to it.

During an orthopaedic surgical procedure, the surgeon may first resect the distal end 518 of the patient's femur 100 to create a surgically-prepared distal surface 592. The surgeon may then secure a pair of fixation pins 588 to the surgically-prepared distal surface 592 of the patient's femur 100, as shown in FIG. 16. To do so, the surgeon may size the patient's femur 100 for the prosthetic femoral component and set the femoral rotation. A procedure for locating fixation pins during a femoral sizing and rotation setting procedure is described in the surgical technique document referred to as SIGMA Fixed Reference Surgical Technique (2010), which is available from DePuy Orthopaedics Inc. After sizing the femoral component and setting the rotation, the surgeon may attach the fixation pins 588 to the surgically-prepared distal surface 592 of the patient's femur 100.

After attaching the fixation pins 588, the surgeon may position the 4-in-1 cutting block 512 on the surgically-prepared distal surface 592 of the patient's femur 100. To do so, the surgeon may align the shafts 594 of the fixation pins 588 with a pair of the guide holes 586 of the 4-in-1 cutting block 512. The surgeon may then advance the 4-in-1 cutting block 512 over the shafts 594 in a direction toward the surgically-prepared distal surface 592 of the patient's femur 100. The bone-engaging surface 522 of the 4-in-1 cutting block 512 contacts the surgically-prepared distal surface 592 when the instrument 510 is positioned on the distal end 518 of the patient's femur 100, as shown in FIG. 17. If the surgeon wishes to relocate the 4-in-1 cutting block 512, the surgeon may use another combination of guide holes 586 to change the position of the cutting block 512 on the patient's femur 100. If additional fixation is necessary, the surgeon may insert additional fixation pins 588 through the guide holes 590 defined in the 4-in-1 cutting block 512.

Once installed in such a manner, the surgeon may use the 4-in-1 cutting block 512 to make a number of resections of the distal end 518 of the patient's femur 100. For example, as shown in FIG. 17, the anterior cutting guide 528 defines a resection plane that extends through the distal end 518 of the patient's femur 100. The surgeon may advance a cutting tool, such as, for example, a surgical cutting saw 596 through the anterior cutting guide 528 to engage the patient's femur 100 and operate the surgical saw 596 to surgically prepare an anterior surface of the patient's femur 100 to receive the prosthetic femoral component. The surgeon may similarly use the posterior cutting guide 534 to resect the posterior condyles 598 of the patient's femur 100 and surgically prepare the posterior surfaces of the patient's femur 100 to receive the prosthetic femoral component.

Figure 18:
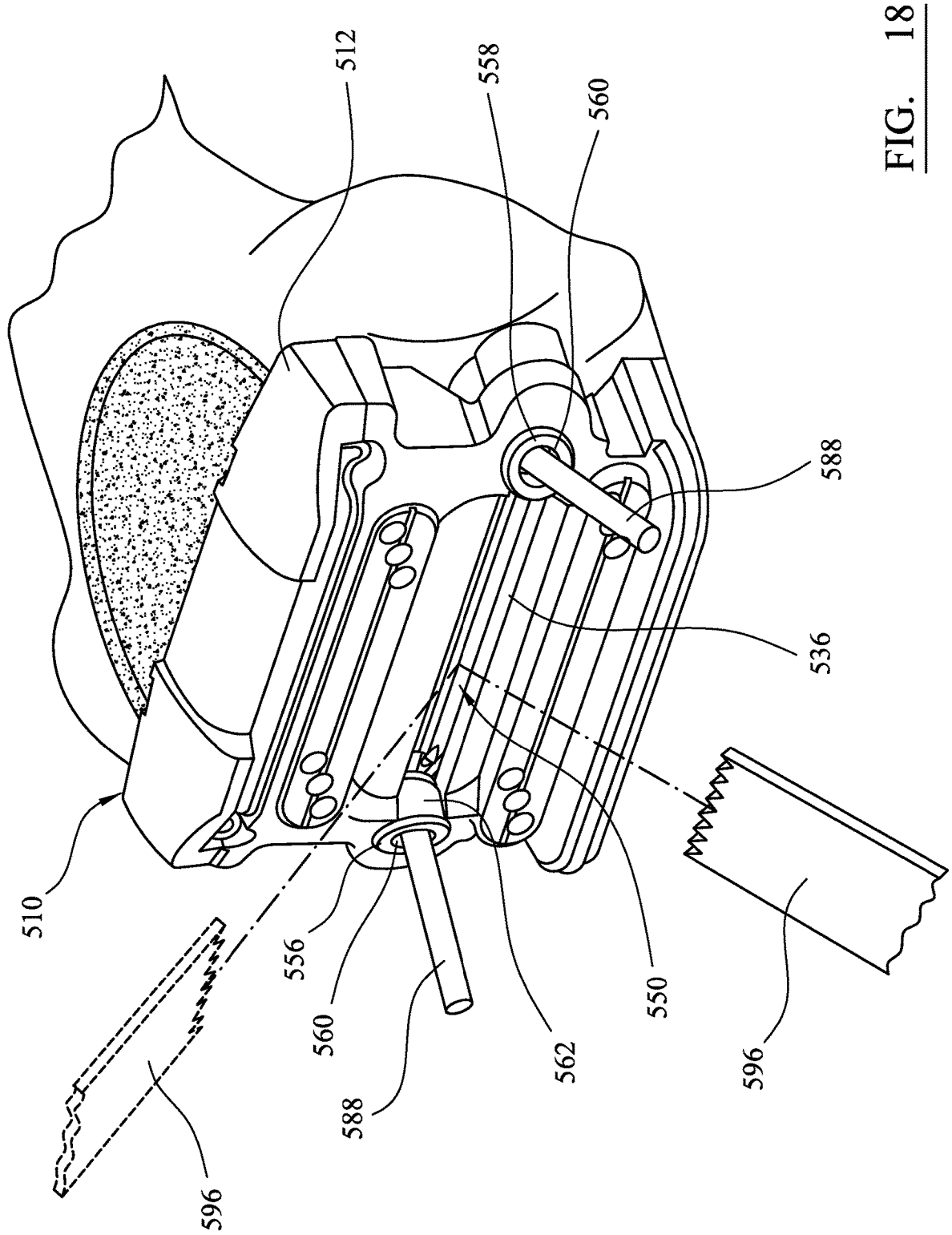
FIG. 18 is a view similar to FIG. 17, but showing the cutting block of FIG. 12 being used to perform the chamfer cuts on the distal end of the patient's femur.

As shown in FIG. 18, the surgeon may also use the captured chamfer cutting guide assembly 550 in cooperation with the planar cutting guides 576, 580 of the wedge component 570 to make chamfer cuts on the patient's femur 100. To do so, the surgeon may first insert fixation pins 588 through the elongated bores 560 of the metallic bushings 556, 558 of the chamfer cutting guide assembly 550. The surgeon may then remove any fixation pins 588 from the guide holes 586, 590 since fixation pins 588 positioned in the guide holes 586, 590 would disrupt the chamfer cutting process. The surgeon may then advance the surgical cutting saw 596 through opening between the cutting guides 552, 576 to guide the saw 596 during performance of the anterior chamfer cut (as shown in solid lines in FIG. 18), and then through the opening between the cutting guides 554, 580 to guide the saw 596 during performance of the posterior chamfer cut (as shown in phantom lines in FIG. 18).

During performance of such chamfer cuts, the metallic cutting guides 552, 554 function as a saw stop to prevent the saw 596 from engaging the polymeric body of the 4-in-1 cutting block 512 that defines the anterior and posterior edges of the chamfer cutting slot 536. Similarly, the outer surfaces 562 of the metallic bushings 556, 558 function as a saw stop to prevent the saw from engaging the polymeric body of the of the 4-in-1 cutting block 512 that defines the medial and lateral edges of the chamfer cutting slot 536. Likewise, the wedge component's metallic cutting guides 576, 580 function as a saw stop to prevent the saw 596 from engaging the wedge-shaped cutting surface 572 of the wedge component 570.

The cutting guide 578 on the anterior side of the wedge component 570 defines the plane 537 of the anterior chamfer cut on the patient's femur. The distance between this plane and a reference line 539 which extends parallel to the plane from the midpoint of the bone facing surface of the wedge component 570, midway between the intersections between the plane of the bone facing surface and the planes of the chamfer cuts, is $G_{Ant}$.

The cutting guide 580 on the posterior side of the wedge component 570 defines the plane 541 of the posterior chamfer cut on the patient's femur. The distance between this plane and a reference line 543 which extends parallel to the plane from the midpoint of the bone facing surface of the wedge component 570, midway between the intersections between the plane of the bone facing surface and the planes of the chamfer cuts, is $G_{Post}$.

A distal reference line is defined at the intersection of the planes 537, 541 of the anterior and posterior chamfer cuts. The point of intersection of the planes, which lies on the reference line, is indicated in the sectional elevation of FIG. 15 by the reference numeral 545. The distance between this reference line and the plane of the bone engaging surface 522 is $G_{Dist}$.

Figure 19:
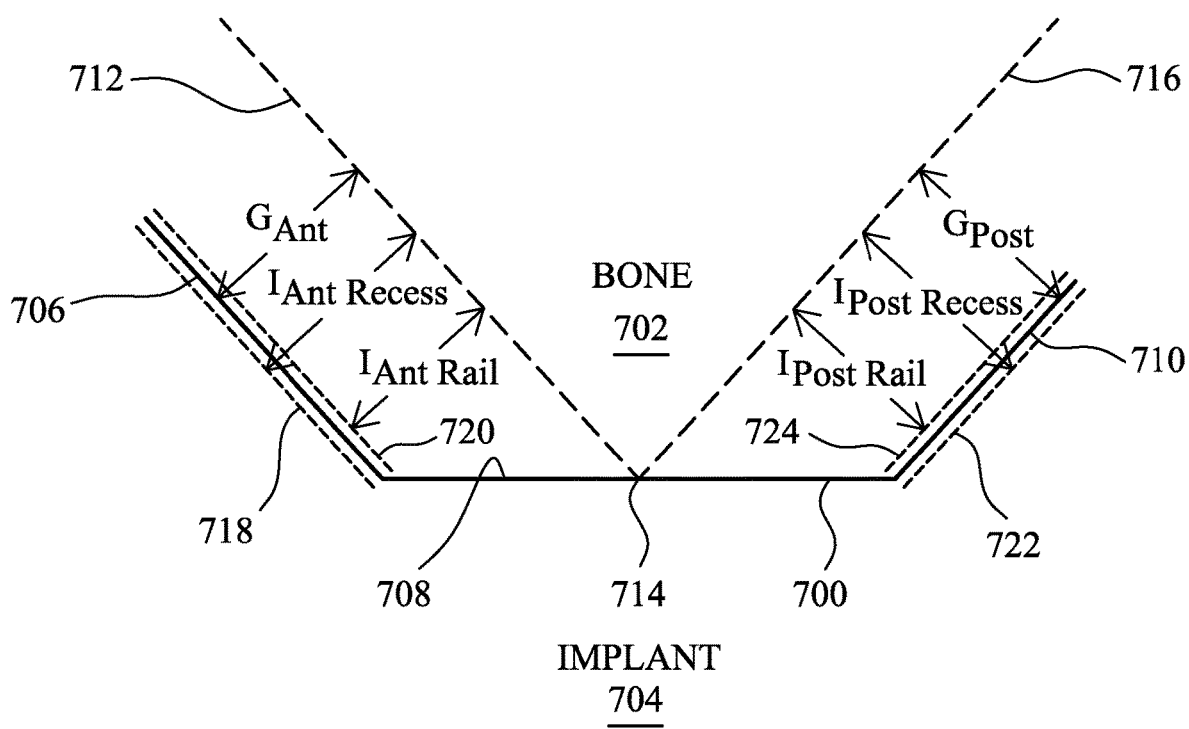
FIG. 19 is a schematic view of the anterior chamfer, distal and posterior chamfer portions of the interface between a patient's femur and a femoral component of a knee joint prosthesis, in which recess and rail features are provided in the anterior chamfer and posterior chamfer portions of the interface.

FIG. 19 is a schematic view of the anterior chamfer, distal and posterior chamfer portions of the interface between a patient's femur and a femoral component of a knee joint prosthesis. A heavy black line represents the interface 700 between the bone 702 and the femoral implant component 704. The interface has anterior chamfer, distal and posterior chamfer portions 706, 708, 710. An anterior reference line 712 extends parallel to the plane of the anterior chamfer portion from the point 714 on the distal portion 708 of the interface, which is equidistant from the anterior and posterior chamfer portions 706, 710. A posterior reference line 716 extends parallel to the plane of the posterior chamfer portion from the point 710 on the distal portion 708 of the interface, which is equidistant from the anterior and posterior chamfer portions 706, 710. The reference lines extend in a plane which is perpendicular to the distal and chamfer portions. The drawing shows the locations of reference lines defined relative to the plane of the chamfer cuts of the femur as well as reference lines which are defined relative to the chamfer portions of the bone facing surface of the femoral component because the locations of these reference lines coincide when the femoral component is properly located on the prepared femur. The distance from the anterior reference line to the plane of the anterior chamfer cut is $G_{Ant}$ and the distance from the posterior reference line to the plane of the posterior chamfer cut is $G_{Post}$.

Recess and rail features are provided on the anterior and posterior chamfer portions of the bone facing surface of the femoral component, as described above with reference to FIGS. 1 to 9. The base of the recess in the anterior chamfer portion of the bone facing surface is spaced apart from the anterior chamfer portion 706 of the surface of the prepared femur, indicated by a dotted line 718. The rails on the anterior chamfer portion of the bone facing surface penetrate surface of the anterior chamfer portion 706 of the surface of the prepared femur, indicated by a dotted line 720. Similarly, the base of the recess in the posterior chamfer portion of the bone facing surface is spaced apart from the posterior chamfer portion 710 of the surface of the prepared femur, indicated by a dotted line 722. The rails on the posterior chamfer portion of the bone facing surface penetrate the surface of the posterior chamfer portion 706 of the surface of the prepared femur, indicated by a dotted line 724. The distance from the anterior reference line 712 to the base 718 of the anterior chamfer recess is $I_{AntRecess}$. The distance from the anterior reference line 712 to the anterior rails is $I_{AntRail}$. The distance from the posterior reference line 716 to the base 722 of the posterior chamfer recess is $I_{PostRecess}$. The distance from the posterior reference line 716 to the posterior rails is $I_{PostRail}$.

The value of $(I_{AntRecess}-G_{Ant})$ is at least about 0.5 mm, for example about 1 mm. The value of $(I_{PostRecess}-G_{Post})$ is at least about 0.5 mm, for example about 1 mm. This is a measure of the size of the gap between the surface of the bone and the base of a recess.

The value of $(G_{Ant}-I_{AntRail})$ is at least about 0.05 mm, for example about 0.5 mm. The value of $(G_{Post}-I_{PostRail})$ is at least about 0.05 mm, for example about 0.5 mm. This is a measure of the depth to which a rail penetrates the surface of the bone.

Figure 20:
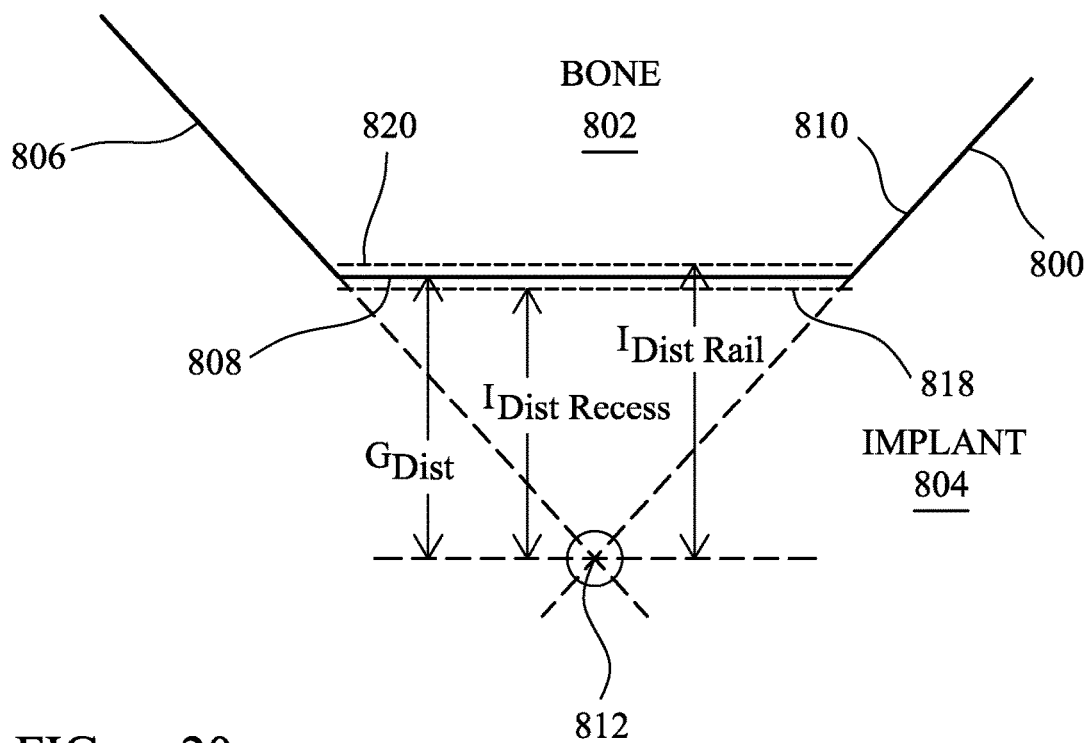
FIG. 20 is a schematic view of the anterior chamfer, distal and posterior chamfer portions of the interface between a patient's femur and a femoral component of a knee joint prosthesis, in which recess and rail features are provided in the distal portion of the interface.

FIG. 20 is a schematic view of the anterior chamfer, distal and posterior chamfer portions of the interface between a patient's femur and a femoral component of a knee joint prosthesis. A heavy black line represents the interface 800 between the bone 802 and the femoral implant component 804. The interface has anterior chamfer, distal and posterior chamfer portions 806, 808, 810. A reference line 812 (extending into the plane of the page on which the drawing is set out) is defined at the intersection of the planes of the anterior and posterior chamfer portions. The drawing shows the location of a reference line defined relative to the plane of the chamfer cuts of the femur as well as a reference line which is defined relative to the chamfer portions of the bone facing surface of the femoral component because the locations of these reference lines coincide when the femoral component is properly located on the prepared femur. The distance from the reference line to the plane of the distal portion 808 of the interface 800 is $G_{Dist}$.

Recess and rail features are provided on the distal portion of the bone facing surface of the femoral component, as described above with reference to FIGS. 10 and 11. The base of the recess in the anterior chamfer portion of the bone facing surface is spaced apart from the distal portion 806 of the surface of the prepared femur, indicated by a dotted line 818. The rails on the distal portion of the bone facing surface penetrate the surface of the distal portion 806 of the surface of the prepared femur, indicated by a dotted line 820. The distance from the reference line 812 to the base 818 of the distal recess is $I_{DistRecess}$. The distance from the anterior reference line 812 to the distal rails is $I_{DistRail}$.

The value of ($G_{Dist}-I_{DistRecess}$) is at least about 0.5 mm, for example about 1 mm. This is a measure of the size of the gap between the surface of the bone and the base of the recess.

The value of ($I_{DistRail}-G_{Dist}$) is at least about 0.05 mm, for example about 0.5 mm. This is a measure of the depth to which the rail penetrates the surface of the bone.

When one or more portions (especially each of the portions) of the bone facing surface of the femoral component is provided by a coating of a material which promotes formation of a strong physical connection with the bone tissue when bone is generated at the interface between the tissue and the coated surface (for example a ceramic hydroxyapatite such as $(Ca_{10}(PO_4)_6(OH)_2)$, measurements are made to the exposed surface of the coating.

Details of a surgical procedure which can be adapted for implantation of a femoral component as provided by the invention can be found in the document entitled Attune Surgical Technique, published by DePuy Orthopaedics Inc in 2011.

The invention claimed is:

1. A method of implanting a femoral component of a knee joint prosthesis on a femur of a patient,
   the femoral component having a bearing surface for articulation with a tibial bearing surface and an opposite bone facing surface, in which the bone facing surface has:
   an anterior portion for engaging the femur on its anterior side,
   a posterior portion for engaging the femur on its posterior side,
   a distal portion for engaging a distal end face of the femur,
   an anterior chamfer portion located between the anterior portion and the distal portion, which is inclined from the distal portion to the anterior portion, and
   a posterior chamfer portion located between the posterior portion and the distal portion, which is inclined from the distal portion to the posterior portion;
   wherein:
   each of the distal, anterior and posterior portions of the bone facing surface has a porous structure to promote bone ingrowth and lacks a rail at any of their edges so that each portion is planar and can form close surface-to-surface contact with adjacent bone surfaces which are planar;
   at least one of the chamfer portions of the bone facing surface of the femoral component has spaced apart medial and lateral rails with at least one recess between them, each rail having a top and the recess having a base spaced from the tops of the rails;
   wherein the method includes:
   resecting the femur to prepare surfaces that correspond to the anterior, distal, posterior, anterior chamfer and posterior chamfer surfaces of the femoral component; and
   implanting the femoral component on the resected femur without the use of cement;
   wherein when the femoral component is implanted on the resected femur there is close surface-to-surface contact between the porous structures of the anterior, distal and posterior portions of the bone facing surface of the femoral component and corresponding surfaces of the femur, the tops of the medial and lateral rails of at least one of the chamfer portions contact the corresponding surface of the patient's femur and there is no cement between the anterior, distal, posterior, anterior chamfer and posterior chamfer portions of the bone facing surface of the femoral component and the corresponding surfaces of the resected femur,
   the rails are provided on the anterior chamfer portion, and
   wherein there is clearance between the patient's femur and the base of the recess in the anterior chamfer portion when the femoral component is positioned on a patient's femur.

2. The method of claim 1 wherein the medial rail is located at a medial edge of the femoral component and the lateral rail is located at a lateral edge of the femoral component.

3. The method of claim 1 wherein each of the medial and lateral rails is tapered inwardly towards its top.

4. The method of claim 1 wherein each of the anterior, distal, posterior, anterior chamfer and posterior chamfer portions of the bone facing surface has a porous structure to promote bone ingrowth without the use of a bone cement.

5. A method of implanting a femoral component of a knee joint prosthesis on a femur of a patient,
   the femoral component having a bearing surface for articulation with a tibial bearing surface and an opposite bone facing surface, in which the bone facing surface has:
   an anterior portion for engaging the femur on its anterior side,
   a posterior portion for engaging the femur on its posterior side,
   a distal portion for engaging a distal end face of the femur,
   an anterior chamfer portion located between the anterior portion and the distal portion, which is inclined from the distal portion to the anterior portion, and
   a posterior chamfer portion located between the posterior portion and the distal portion, which is inclined from the distal portion to the posterior portion;
   wherein:
   each of the distal, anterior and posterior portions of the bone facing surface has a porous structure to promote bone ingrowth and lacks a rail at any of their edges so that each surface is planar and can form close surface-to-surface contact with adjacent bone surfaces which are planar;
   at least one of the chamfer portions of the bone facing surface of the femoral component has spaced apart medial and lateral rails with at least one recess between them, each rail having a top and the recess having a base spaced from the tops of the rails;
   wherein the method includes:
   resecting the femur to prepare surfaces that correspond to the anterior, distal, posterior, anterior chamfer and posterior chamfer surfaces of the femoral component; and
   implanting the femoral component on the resected femur without the use of cement;
   wherein when the femoral component is implanted on the resected femur there is close surface-to-surface contact between the porous structures of the anterior, distal and posterior portions of the bone facing surface of the femoral component and corresponding surfaces of the femur, the tops of the medial and lateral rails of at least one of the chamfer portions contact the corresponding surface of the patient's femur and there is no cement between the anterior, distal, posterior, anterior chamfer and posterior chamfer portions of the bone facing surface of the femoral component and the corresponding surfaces of the resected femur, wherein the rails are provided on the posterior chamfer portion, and wherein there is clearance between the patient's femur and the base of the recess in the posterior chamfer portion when the femoral component is positioned on a patient's femur.

6. A method of implanting a femoral component of a knee joint prosthesis on a femur of a patient, the femoral component having a bearing surface for articulation with a tibial bearing surface and an opposite bone facing surface, in which the bone facing surface has:

an anterior portion for engaging the femur on its anterior side, a posterior portion for engaging the femur on its posterior side, a distal portion for engaging a distal end face of the femur, an anterior chamfer portion located between the anterior portion and the distal portion, which is inclined from the distal portion to the anterior portion, and a posterior chamfer portion located between the posterior portion and the distal portion, which is inclined from the distal portion to the posterior portion;

wherein:

each of the distal, anterior and posterior portions of the bone facing surface has a porous structure to promote bone ingrowth and lacks a rail at any of their edges so that each surface is planar and can form close surface-to-surface contact with adjacent bone surfaces which are planar;

at least one of the chamfer portions of the bone facing surface of the femoral component has spaced apart medial and lateral rails with at least one recess between them, each rail having a top and the recess having a base spaced from the tops of the rails;

wherein the method includes:

resecting the femur to prepare surfaces that correspond to the anterior, distal, posterior, anterior chamfer and posterior chamfer surfaces of the femoral component; and implanting the femoral component on the resected femur without the use of cement;

wherein when the femoral component is implanted on the resected femur there is close surface-to-surface contact between the porous structures of the anterior, distal and posterior portions of the bone facing surface of the femoral component and corresponding surfaces of the femur, the tops of the medial and lateral rails of at least one of the chamfer portions contact the corresponding surface of the patient's femur and there is no cement between the anterior, distal, posterior, anterior chamfer and posterior chamfer portions of the bone facing surface of the femoral component and the corresponding surfaces of the resected femur, wherein the rails are provided on both the anterior chamfer portion and the posterior chamfer portion, and wherein there is clearance between the patient's femur and the base of the recess in the anterior chamfer surface when the femoral component is positioned on a patient's femur; and wherein there is clearance between the patient's femur and the base of the recess on the posterior chamfer surface when the femoral component is positioned on a patient's femur.

* * * * *